United States Patent
Hamer et al.

(10) Patent No.: US 9,192,648 B2
(45) Date of Patent: Nov. 24, 2015

(54) METHOD OF TREATING MYASTHENIA GRAVIS

(75) Inventors: John Hamer, Reading (GB); Wynne Weston-Davies, Reading (GB)

(73) Assignee: Volution Immuno Pharmaceuticals SA (CH)

( * ) Notice: Subject to any disclaimer, the term of this patent is extended or adjusted under 35 U.S.C. 154(b) by 1397 days.

(21) Appl. No.: 11/991,690

(22) PCT Filed: Sep. 5, 2006

(86) PCT No.: PCT/GB2006/003265
§ 371 (c)(1),
(2), (4) Date: Mar. 30, 2009

(87) PCT Pub. No.: WO2007/028968
PCT Pub. Date: Mar. 15, 2007

(65) Prior Publication Data
US 2009/0209459 A1    Aug. 20, 2009

(30) Foreign Application Priority Data
Sep. 9, 2005   (GB) .................................. 0518443.7

(51) Int. Cl.
A61K 38/17       (2006.01)
A61K 38/00       (2006.01)

(52) U.S. Cl.
CPC ....................................... *A61K 38/17* (2013.01)

(58) Field of Classification Search
CPC ............................................... C12N 2015/8563
See application file for complete search history.

(56) References Cited

U.S. PATENT DOCUMENTS

| | | | | |
|---|---|---|---|---|
| 5,041,389 | A * | 8/1991 | Lindstrom | 436/518 |
| 5,858,969 | A * | 1/1999 | Marsh et al. | 514/1.5 |
| 6,103,748 | A * | 8/2000 | Bryan | 514/400 |
| 7,884,066 | B2 | 2/2011 | Ting | |
| 7,884,069 | B2 | 2/2011 | Schaebitz et al. | |
| 2004/0014782 | A1* | 1/2004 | Krause | 514/313 |
| 2007/0048248 | A1* | 3/2007 | Benedict et al. | 424/78.3 |
| 2007/0141573 | A1 | 6/2007 | Nunn | |
| 2008/0114055 | A1* | 5/2008 | Kiss | 514/437 |
| 2008/0199484 | A1* | 8/2008 | Yu et al. | 424/184.1 |
| 2010/0105611 | A1 | 4/2010 | Hamer | |
| 2011/0059885 | A1 | 3/2011 | Lea et al. | |

FOREIGN PATENT DOCUMENTS

| | | |
|---|---|---|
| WO | WO-93/17099 A1 | 9/1993 |
| WO | WO2004106369 A2 * | 12/2004 |
| WO | 2005023866 | 3/2005 |
| WO | 2005079363 | 9/2005 |
| WO | WO-2007/028968 A1 | 3/2007 |
| WO | WO-2007/117241 A1 | 10/2007 |
| WO | WO-2008/029167 A1 | 3/2008 |
| WO | WO-2008/029169 A2 | 3/2008 |
| WO | WO-2009/098454 A2 | 8/2009 |

OTHER PUBLICATIONS

Copland et al. (2010)Systemic and local anti-C5 therapy reduces the disease severity in experimental autoimmune uveoretinitis, Clin. Exp. Immunol., vol. 159, No. 3, pp. 303-314.*
Piddlesden et al. (1996) Soluble complement receptor 1 (sCR1) protects against experimental autoimmune myasthenia gravis, J. Neuroimmunol., vol. 71, No. 1-2, pp. 173-177.*
Hsu et al. (2003) Chronic progression of tubulointerstitial damage in proteinuric renal disease is mediated by complement activation: a therapeutic role for complement inhibiton, J. Am. Soc. Nephroi., vol. 14, S186-S191.*
Takata et al. (1987) Covalent association of C3b with C4b within C5 convertase of the classical complement pathway, Exp. Med., vol. 165, No. 6, pp. 1494-1507.*
Honor Society of Nursing (2011, updated) "Can Myasthenia gravis be preventable?", www.sharecare.com/question/can-myasthenia-gravis-be-prevented, pp. 1-3.*
Article Sphere.com (2011, updated) "The Effects of Physiotherapy on Neurological Conditions", www.articlesphere.com/Article/The-Effects-of-Physiotherapy-on-Neurological-Conditions/208837, pp. 1-4.*
Xu et al. (2012) Divergenece of duplicate genes in exon-intron structure, Proc. Natl. Acad. Sci. USA, 1109047109, Early Edition, pp. 1-6.*
Banda et al. (2002) Mechanisms of effects of complement inhibition in murine collagne-induced arthritis, Arthr. Rheumatism, vol. 46, pp. 3065-3075.*
Christadoss, "C5 gene influences the development of murine *myasihenia gravis*", The Journal of Immunology, 1988, vol. 140, No. 8, pp. 2589-2592.
Excerpt from The Merck Manual, 1999, pp. 1500-1501; and English translation thereof.
Harris et al., "Coupling complement regulators to immunoglobulin domains generates effective anti-complement reagents with extended half-life in vivo", Clin Exp Immunol, 2002, 129, 198-207.
Hepburn et al., "Prevention of experimental autoimmune myasthenia gravis by rat Crry-Ig: A model agent for long-term complement inhibition in vivo", Molecular Immunology, 2008, 45, 395-405.
Nunn et al., "Complement inhibitor of C5 activation from the soft tick Ornithodorus moubata", The Journal of Immunology, 2005, 174, 2084-2091.
Richman et al., "Antibody effector mechanisms in myasthenia gravis The complement hypothesis", Annals of the New York Academy of Sciences, 1998, 450-465.

(Continued)

*Primary Examiner* — Manjunath Rao
*Assistant Examiner* — Samuel Liu
(74) *Attorney, Agent, or Firm* — Choate, Hall & Stewart LLP; Fangli Chen; Stephanie L. Schonewald

(57) ABSTRACT

The invention relates to the use of agents that bind the complement protein C5 in the treatment of diseases associated with inappropriate complement activation, and in particular in the treatment of myasthenia gravis.

14 Claims, 18 Drawing Sheets

(56) References Cited

OTHER PUBLICATIONS

Sahu et al., "Complement inhibitors: a resurgent concept in anti-inflammatory therapeutics", Immunopharmacology, 2000, 49, 133-148.
Soltys et al., "Novel complement inhibitor limits severity of experimentally myasthenia gravis", Ann Neurol, 2009, 65, 67-75.
Asghar et al., Inhibition of Complement by a Series of Substituted 2-Aryl-1, 3-Indandiones: Interaction with the Fifth Component of Complement, Molecular Immunology, 23:459-465 (1986).
Astigarraga et al., Host immune response evasion strategies in Ornithodoros erraticus and O. moubata and their relationship to the development of an antiargasid vaccine, Parasite Immunology, 19:401-410 (1997).
Bao et al., Transgenic Expression of a Soluble Complement Inhibitor Protects Against Renal Disease and Promotes Survival in MRUIpr Mice, Journal of Immunology, 168:3601-3607 (2002).
Baranda et al., Purification, N-terminal sequencing and diagnostic value of the major antigens of Ornithodoros erraticus and O. moubata, Veterinary Parasitology, 87:193-206 (2000).
Bedford, J.M. and Witkin, S.S., Influence of complement depletion on sperm function in the female rabbit, Journal of Reproductive Fertility, 69:523-528 (1983).
Biesecker, G. et al., Derivation of,RNA aptamer inhibitors of human complement C5, Immunopharmacology, 42:219-230 (1999).
Bumpers, H.L. and Baum, J., The Effect of a Novel C5 Inhibitor (K-76 COONa) on Tumor Cell Chemotaxis, Journal of Laboratory and Clinical Medicine, 102(3):421-427 (1983).
Cicchetti et al., Combined Inhibition of Apoptosis and Complement Improves Neural Graft Survival of Embryonic Rat and Porcine Mesencephalon in the Rat Brain, Experimental Neurology, 177:376-384 (2002).
Diamond et al., Human CD59 expressed in transgenic mouse hearts inhibits the activation of complement, 3:305-312 (1995).
Ember et al., Characterization of Complement Anaphylatoxins and Their Biological Responses, In: The Human Complement System in Health and Disease, Volanakis, J.E., Frank, M.M. (Eds.), Marcel Dekker, New York, 241-284.
Evans et al., In Vitro and In Vivo Inhibition of Complement Activity by a Single-chain Fv Fragment Recognizing human C5, Molecular Immunology, 32(16): 1183-1195 (1995).
Fecke et al., Protection of hDAF-transgenic porcine endothelial cells against activation by human complement: role of the membrane attack complex, Xenotransplantation, 9:97-105 (2002).
Feuillard et al., Comparative study of in vitro inhibition of activation of the classical and alternative pathways of human complement by the magnesium and sodium salts of the anti-inflammatory peptide N-acetyl-aspartyl-glutamic acid (NAAGA), Agent and Actions, 32:343-346 (1991).
Fiorante et al., Low molecular weight dextran sulfate prevents complement activation and delays hyperacute rejection in pig-to-human xenotransplantation models, Xenotransplantation, 8:24-35 (2001).
Fitch et al., Pharmacology and Biological Efficacy of a Recombinant, Humanized, Single-Chain Antibody C5 Complement Inhibitor in Patients Undergoing Coronary Artery Bypass Graft Surgery With Cardiopulmonary Bypass, Circulation, 100:2499-2506 (1999).
Frei et al., Generation of a monoclonal antibody to mouse C5 application in an ELISA assay for detection of anti-05 antibodies, Molecular Cellular Probes, 1:141-149 (1987).
Giclas, P.C., Classical pathway evaluation and alternative pathway evaluation (sections 13.1. And 13.2), In: Current Protocols in Immunology, Editors: J.E. Coligan, A.M. Kruisbeek, D.H. Marguiles, E.M. Shevach and W. Strober, vol. 3 (1994).
Hebell et al., Suppression of the Immune Response by a Soluble Complement Receptor of B Lymphocytes, 254:102-105 (1991).
Homeister et al., Effects of Complement Activation in the Isolated Heart, Circulation Research, 71:303-319 (1992).

Jarvis et al., IgM rheumatoid factor and the inhibition of covalent binding of C4b to IgG in immune complexes, Clinical Experimental Rheumatology, 11:135-141 (1993).
Keller et al., Cloning of the cDNA and Expression of Moubatin, an Inhibitor of Platelet Aggregation, Journal of Biological Chemistry, 268:5450-5456 (1993).
Konttinen et al., Complement in acute and chronic arthritides: assessment of C3c, C9 and protectin (CD59) in synovial membrane, Ann. Rheum. Dis., 55:888-894 (1996).
Kopf, M. et al., Complement component C3 promotes T-cell priming and lung migration to control acute influenza virus infection, Nature Medicine, 8:373-378 (2002).
Kroshus et al., A recombinant soluble chimeric complement inhibitor composed of human CD46 and CD55 reduces acute cardiac tissue injury in models of pig-to-human heart transplantation, Transplantation, 69:2282-2289 (2000).
Köhl, J., Anaphylatoxins and infectious and non-infectious inflammatory diseases, Molecular Immunology, 38;175-187 (2001).
Link et al., Selection of phage-displayed anti-guinea pig C5 or C5a antibodies and their application in xenotransplantation, Molecular Immunology, 36:1235-1247 (1999).
Mans et al., Identification of putative proteins involved in granule biogenesis of tick salivary glands, Electrophoresis, 22:1739-1746 (2001).
Mans et al., Pathogenic mechanisms of sand tampan toxicoses induced by the tick, Ornithodoros savignyi, Toxicon, 40:1007-1016 (2002).
McKenzie et al., Regulation of Complement Activity by Vaccinia Virus Complement-Control Protein, Journal of Infectious Diseases, 166:1245-1250 (1992).
Miletic, V.D. and Popovic, O., Complement activation in stored platelet concentrates, Transfusion, 33:150-154 (1993).
Mulligan, M. et al., Endothelial Targeting and Enhanced Anti-inflammatory Effects of Complement Inhibitors Possessing Sialyl Lewis' Moieties, Journal of Immunology, 162:4952-4959 (1999)
Paesen et al., Tick Histamine-Binding Proteins: Isolation, Cloning, and Three-Dimensional Structure, Molecular Cell, 3:661-671 (1999).
Paesen et al., Tick histamine-binding proteins: lipocalins with a second binding cavity, Biochimica et Biophysica Acta, 1482:92-101 (2000).
Pratt et al., Effects of Complement Inhibition with Soluble Complement Receptor-1 on Vascular Injury and Inflammation during Renal Allograft Rejection in the Rat, American Journal of Pathology, 149:2055-2066 (1996).
Rehrig et al., Complement Inhibitor, Complement Receptor 1-Related Gene/Protein y-lg—Attenuates Intestinal Damage After the Onset of Mesenteric Ischemia/Reperfusion Injury in Mice, Journal of Immunology, 167:5921-5927 (2001).
Ribeiro, Ixodes dammini: Salivary Anti-complement Activity, Experimental Parasitology, 64:347-353 (1987).
Rinder et al., Blockade of C5a and C5b-9 Generation Inhibits Leukocyte and Platelet Activation during Extracorporeal Circulation, Journal of Clinical Investigation, 96: 1564-1572 (1995).
Rollins et al., Anti-C5 Single Chain Antibody Therapy Blocks Complement & Leukocyte Activation and Reduces Myocardial Tissue Damage in CPB Patients, Molecular Immunology, 35:397-397 (1998).
Rollins et al., Retrovital Vector Producer Cell Killing in Human Serum Is Mediated by Natural Antibody and Complement: Strategies for Evading the Humoral Immune Response, Human Gene Therapy, 7:619-626 (1996).
Sandoval et al., Distal Recognition Site for Classical Pathway Convertase Located in the C345C/Netrin Module of Complement Component C5, The Journal of Immunology, 165:1066-1073 (2000).
Schiller et al., Expression of a Soluble Complement Inhibitor Protects Transgenic Mice from Antibody-Induced Acute Renal Failure, Journal of the American Society of Nephrology, 12:71-79 (2001).
Seffernick et al, Melamine deaminase and atrazine chlorohydrolase: 98 percent identical but functionally different, J. Bacteriology, 183:2405-2410 (2001).
Smith et al., Membrane-targeted complement inhibitors, Molecular Immunology, 38:249-255 (2001).

(56) References Cited

OTHER PUBLICATIONS

Sodetz, J. and Plumb, M. et al., Complement: Terminal Pathway, Encyclopedia of Life Sciences, p. 1-6 (2001).

Solomon et al., Transmission of antibody-induced arthritis is independent of complement component 4(C4) and the complement receptors 1 and 2 (CD21/35), European Journal of Immunology, 32:644-651 (2002).

Tanaka et al., Effect of Anti-complement Agent K76 COOH on Hamster-To-Rat and Guinea Pig-to-Rat Heart Xenotransplantation, Transplantation, 62:681-688 (1996).

Thomas et al., Sulfonated Dextran Inhibits Complement Activation and Complement Dependent Cytotoxicity in an in vitro Model of Hyperacute Xenograft Rejection, Molecular Immunology, 33:643-648 (1996).

Vakeva et al., Myocardial Infarction and Apoptosis After Myocardial Ischemia and Reperfusion-Role of the Terminal Complement Components and Inhibition by Anti-05 Therapy, Circulation, 97:2259-2267 (1998).

Valenzuela et al., Purification, Cloning, and Expression of a Novel Salivary Anti-complement Protein from the Tick, Ixodes scapularis, Journal of Biology Chemistry, 275:18717-18723 (2000).

Wang et al., Amelioration of lupus-like autoimmune disease in NZB/WF, mice after treatment with a blocking monoclonal antibody specific for complement component C5, Proceedings of the National Academy of Science USA, 93:8563-8568 (1996).

Wang et al., Anti-C5 monoclonal antibody therapy prevents collagen-induced arthritis and ameliorates established disease, Proceedings of the National Academy of Science USA, 92:8955-8959 (1995).

Ward et al., Use of Animal Models to Define Complement Functions, In: Contemporary Immunology: Therapeutic Interventions in the Complement System, Lambris, J.D., Holers, V.M. (Eds.), Humana Press, Totowa, NJ, 237-253 (2000).

Weisman et al., Soluble Human Complement Receptor Type 1: In vivo Inhibitor of Complement Suppressing Post-Ischemic Myocardial Inflammation and Necrosis, Science, 249:146-151 (1990).

Wells, James A., Additivity of Mutational Effects in Proteins, Biochemistry 29(37):8509-8517 (1990).

White, Jr. et al., Suppression of mouse complement activity by contaminants of technical grade pentachlorophenol, Agents and Actions, 16:385-392 (1985).

Wyss-Coray et al., Prominent neurodegeneration and increased plaque formation in complement-inhibited Alzheimer's mice, Proceedings of the National Academy of Science USA, 99:10837-10842 (2002).

Zhang et al., Targeting of Functional Antibody-Decay-accelerating Factor Fusion Proteins to a Cell Surface, Journal of Biology Chemistry, 276:27290-27295 (2001).

\* cited by examiner

FIG. 2

```
ATGCTGGTTTTGGTGACCCTGATTTTCTCCTTTTCTGCAACATGGCATATGCTGACAGC   60
 M  L  V  L  V  T  L  I  F  S  F  S  A  N  I  A  Y  A  D  S    20

GAAAGCGACTGCACTGGAAGCGAACCTGTTGACGCCTTCCAAGCTTTCAGTGAGGGCAAA  120
 E  S  D  C  T  G  S  E  P  V  D  A  F  Q  A  F  S  E  G  K    40

GAGGCATATGTCCTGGTGAGGTCCACGGATCCCAAAGGAGGACTGCTTGAAAGGAGAA  180
 E  A  Y  V  L  V  R  S  T  D  P  K  A  R  D  C  L  K  G  E    60

CCAGCCGGAGAAAAGCAGGACAACACGTTGCCGGTGATGATGACGTTTAAGAATGGCACA  240
 P  A  G  E  K  Q  D  N  T  L  P  V  M  M  T  F  K  N  G  T    80

GACTGGGCTTCAACCGATTGGACGTTTACTTTGGACGGTGCAAAGGTAACGGCAACCCTT  300
 D  W  A  S  T  D  W  T  F  T  L  D  G  A  K  V  T  A  T  L   100

GGTAACCTAACCCAAAATAGGGAAGTTGTCTACGACTCGCAAAGTCATCACTGCCACGTT  360
 G  N  L  T  Q  N  R  E  V  V  Y  D  S  Q  S  H  H  C  H  V   120

GACAAGGTCGAGAAGGAAGTTCCAGATTATGAGATGTGGATGCTCGATGCGGAGGGCTT  420
 D  K  V  E  K  E  V  P  D  Y  E  M  M  L  D  A  G  G  L   140

GAAGTGGAAGTCGAGTGCTGCCGTCAAAGCTTGAAGAGTTGGCGTCTGGCAGGAACCAA  480
 E  V  E  V  E  C  C  R  Q  K  L  E  E  L  A  S  G  R  N  Q   160

ATGTATCCCCATCTCAAGGACTGCTAG                                   507
 M  Y  P  H  L  K  D  C  *                                    168
```

Anion exchange chromatography

Time [minutes]

Classical haemolytic assay of fra

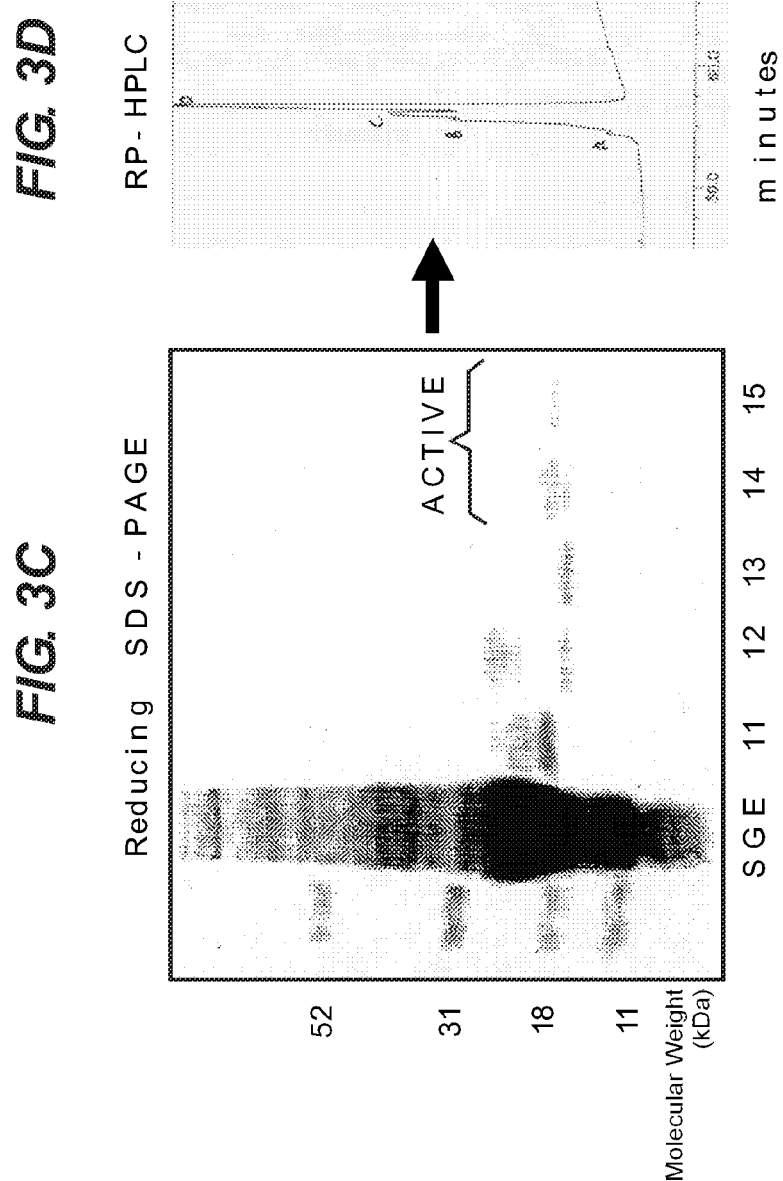

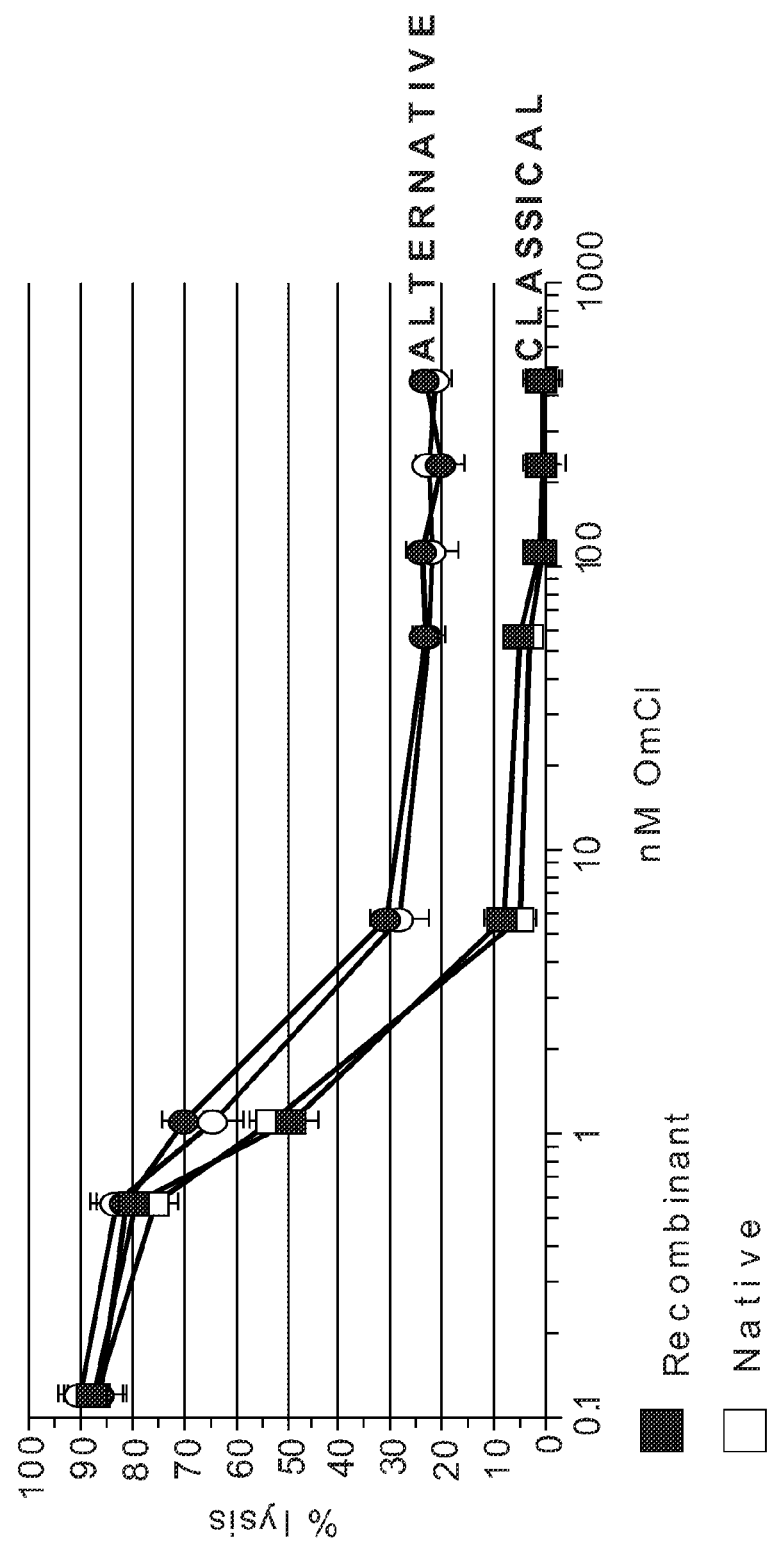
*FIG. 5A* Recombinant EV576

FIG. 6C

| Hours p.i. | 0 | 6 | 24 | 30 | 52 | 72 | 100 | 122 | 155 | 163 |
|---|---|---|---|---|---|---|---|---|---|---|
| Cage A (PBS) | | | | | | | | | | |
| 0 | 0 | 0 | 2 | 2.5 | 3.5 | 4 | 4 | 4 | 4 | 4 |
| 1 | 0 | 0 | 1 | 2 | 4 | 4 | 4 | 4 | 4 | 4 |
| 2 | 0 | 0 | 1.5 | 2.5 | 3.5 | 4 | 4 | 4 | 4 | 4 |
| 3 | 0 | 0 | 2 | 2 | 3 | 4 | 4 | 4 | 4 | 4 |
| 4 | 0 | 0 | 1.5 | 2 | 3 | 4 | 4 | 4 | 4 | 4 |
| 5 | 0 | 0 | 2 | 2 | 3.5 | 4 | 4 | 4 | 4 | 4 |
| Average | 0 | 0 | 1.666667 | 2.166667 | 3.416667 | 4 | 4 | 4 | 4 | 4 |
| Cage D (rEV576) | | | | | | | | | | |
| 0 | 0 | 0 | 0 | 0 | 0 | 0 | 0 | 0 | 0 | 0 |
| 1 | 0 | 0 | 0 | 0 | 0 | 0 | 0 | 0 | 0 | 0 |
| 2 | 0 | 0 | 0 | 0 | 0 | 0 | 0 | 0 | 0 | 0 |
| 3 | 0 | 0 | 0 | 0 | 0 | 0 | 0 | 0 | 0 | 0 |
| 4 | 0 | 0 | 0 | 0 | 0 | 0 | 0 | 0 | 0 | 0 |
| 5 | 0 | 0 | 0 | 0 | 0 | 0 | 0 | 0 | 0 | 0 |
| Average | 0 | 0 | 0 | 0 | 0 | 0 | 0 | 0 | 0 | 0 |

METHOD OF TREATING MYASTHENIA GRAVIS

CROSS REFERENCE TO RELATED APPLICATIONS

The present application is a National Stage Application claiming the priority of co-pending PCT Application No. PCT/GB2006/003265 filed Sep. 5, 2006, which in turn, claims priority from Great Britain Application Serial No. 0518443.7, filed Sep. 9, 2005. Applicants claim the benefits of 35 U.S.C. §120 as to the PCT application and priority under 35 U.S.C. §119 as to the said Australian application, and the entire disclosures of both applications are incorporated herein by reference in their entireties.

The present invention relates to the use of agents that bind the complement protein C5 in the treatment of diseases associated with inappropriate complement activation, and in particular in the treatment of myasthenia gravis.

All documents mentioned in the text and listed at the end of this description are incorporated herein by reference.

BACKGROUND TO THE INVENTION

The complement system is an essential part of the body's natural defence mechanism against foreign invasion and is also involved in the inflammatory process. More than 30 proteins in serum and at the cell surface are involved in complement system function and regulation. Recently it has become apparent that, as well as the ~35 known components of the complement system which may be associated with both beneficial and pathological processes, the complement system itself interacts with at least 85 biological pathways with functions as diverse as angiogenesis, platelet activation, glucose metabolism and spermatogenesis (Mastellos, D., et al., Clin Immunol, 2005. 115(3): p. 225-35).

The complement system is activated by the presence of foreign antigens. Three activation pathways exist: (1) the classical pathway which is activated by IgM and IgG complexes or by recognition of carbohydrates; (2) the alternative pathway which is activated by non-self surfaces (lacking specific regulatory molecules) and by bacterial endotoxins; and (3) the lectin pathway which is activated by binding of manna-binding lectin (MBL) to mannose residues on the surface of a pathogen. The three pathways comprise parallel cascades of events that result in the production of complement activation through the formation of similar C3 and C5 convertases on cell surfaces resulting in the release of acute mediators of inflammation (C3a and C5a) and formation of the membrane attack complex (MAC). The parallel cascades involved in the classical and alternative pathways are shown in FIG. 1.

Complement can be activated inappropriately under certain circumstances leading to undesirable local tissue destruction. Inappropriate complement activation has been shown to play a role in a wide variety of diseases and disorders including acute pancreatitis, Alzheimer's disease, allergic encephalomyelitis, allotransplatation, asthma, adult respiratory distress syndrome, burn injuries, Crohn's disease, glomerulonephritis, haemolytic anaemia, haemodialysis, hereditary angioedema, ischaemia reperfusion injuries, multiple system organ failure, multiple sclerosis, myasthenia gravis, ischemic stroke, myocardial infarction, psoriasis, rheumatoid arthritis, septic shock, systemic lupus erythematosus, stroke, vascular leak syndrome, transplantation rejection and inappropriate immune response in cardiopulmonary bypass operations. Inappropriate activation of the complement system has thus been a target for therapeutic intervention for many years and numerous complement inhibitors targeting different parts of the complement cascade are under development for therapeutic use.

In ischemic stroke and myocardial infarction, the body recognises the dead tissue in the brain or heart as foreign and activates complement so causing further local damage. Similarly in cardiopulmonary bypass operations, the body recognises the plastic surfaces in the machine as foreign, activates complement and can result in vascular damage. In autoimmune diseases, the body may wrongly recognise itself as foreign and activate complement with local tissue damage (e.g. joint destruction in rheumatoid arthritis and muscle weakness in myasthenia gravis).

Myasthenia gravis is a chronic autoimmune disease that results in progressive fatigue, loss of muscle tone and increasing paralysis. These symptoms are caused by inappropriate activation of complement resulting in an immune response directed against the nicotinic acetylcholine receptor (AchR) which leads, in turn, to reduced neuromuscular transmission. Myasthenia gravis may occur in association with other diseases such as a thymic tumor or thyrotoxicosis, as well as with rheumatoid arthritis and lupus erythematosus.

There is currently no cure for myasthenia gravis. The disease is usually treated initially using anticholinesterase agents, such as neostigmine bromide (Prostigmin) and pyridostigmine bromide (Mestinon), which help improve neuromuscular transmission and increase muscle strength. Treatment with anticholinesterase agents is, however, associated with adverse side effects caused from acetylcholine accumulation including gastrointestinal complaints and increased bronchial and oral secretions. In addition, although anticholinesterase agents often provide symptomatic benefit, they do not influence the course of the disease. Patients who do not respond to anticholinerterase agents may also be treated with long-term immunosuppressive drugs such as the cortocosteroid prednisone, or other immunosuppressant drugs such as cyclosporine, azathioprine and cyclophosphamide. These immunosuppressant drugs are, however, associated with serious side effect. Corticosteroids side effects include weight gain, osteoporosis, hypertension and glaucoma. Azathioprine and cyclosporine are associated with liver dysfunction and an increased risk of malignancy. In some cases, thymectomy is recommended as an alternative to drugs but the response is unpredictable and symptoms of the disease may continue for months or years after surgery.

Experimental autoimmune myasthenia gravis (EAMG) may be induced in animal models by immunisation with purified AChR or anti-AChR antibodies and these models are useful in assessing the effect of complement inhibitors on the progression of the disease. The complement inhibitor soluble complement receptor 1 (sCR1) has been shown to delay weight loss and reduce clinical signs of EAMG, suggesting that this molecule may be useful in the treatment for myasthenia gravis (Piddlesden et al, J. Neuroimmunol., 1996, 71: 173-177). However, daily injections of sCR1 were required to achieve these effects and, although sCR1 reduced weight loss, it did not completely prevent it. sCR1 does not therefore completely prevent the symptoms of myasthenia gravis.

Furthermore, sCR1 acts by binding early products of the complement cascade, C3b and C4b. The complement system plays an important and valuable role in defence against pathogens and many of the early by-products of the cascade are important in the recognition and opsonisation of pathogenic organisms. For this reason, therapeutic intervention in the earlier stages of the classical and alternative pathways is considered to carry the risk of increased susceptibility to microbial infection (Roos, A., et al., Immunobiology, 2002, 205(4-5): p. 595-609).

There is thus a great need for agents that improve upon the currently available treatments for myasthenia gravis.

SUMMARY OF THE INVENTION

Accordingly, the invention provides a method of treating or preventing myasthenia gravis comprising administering to a subject in need thereof a therapeutically or prophylactically effective amount of an agent that binds complement C5.

The invention also provides the use of a therapeutically or prophylactically effective amount of an agent that binds complement C5 in the manufacture of a medicament for treating or preventing myasthenia gravis.

Preferably, the agent acts to prevent the cleavage of complement C5 by C5 convertase into complement C5a and complement C5b-9.

The complement C5 protein, also referred to herein as C5, is cleaved by the C5 convertase enzyme, itself formed from C3a, an earlier product of the alternative pathway (FIG. 1). The products of this cleavage include an anaphylatoxin C5a and a lytic complex C5b-9 also known as membrane attack complex (MAC). C5a is a highly reactive peptide implicated in many pathological inflammatory processes including neutrophil and eosinophil chemotaxis, neutrophil activation, increased capillary permeability and inhibition of neutrophil apoptosis (Guo, R. F. and P. A. Ward, Annu Rev Immunol, 2005, 23: p. 821-52).

MAC is associated with other important pathological processes including rheumatoid arthritis (Neumann, E., et al., Arthritis Rheum, 2002. 46(4): p. 934-45; Williams, A. S., et al., Arthritis Rheum, 2004, 50(9): p. 3035-44), proliferative glomerulonephritis (Quigg, R. J., Curr Dir Autoimmun, 2004. 7: p. 165-80, idiopathic membranous nephropathy (Papagianni, A. A., et al., Nephrol Dial Transplant, 2002, 17(1): p. 57-63), proteinurea (He, C., et al., J Immunol, 2005. 174(9): p. 5750-7), demyelination after acute axonal injury (Mead, R. J., et al., J Immunol, 2002. 168(1): p. 458-65) and is also responsible for acute graft rejection following xenotransplantation (Nakashima, S., et al., J Immunol, 2002. 169(8): p. 4620-7).

C5a has become a target of particular interest in the field of complement-associated disorders (Mizuno, M. and D. S. Cole, Expert Opin Investig Drugs, 2005. 14(7): p. 807-21). Although C5a has many well-recognised pathological associations, the effects of its depletion in humans appear to be limited. Monoclonal antibodies and small molecules that bind and inhibit C5a or C5a receptors have been developed to treat various autoimmune diseases. These molecules do not, however, prevent the release of MAC.

In contrast, administration of an agent that binds C5 according to the first aspect of the invention, inhibits both the C5a peptide and the MAC. Surprisingly, it has been found that inhibition of both C5a and the MAC completely attenuates clinical symptoms associated with myasthenia gravis. Furthermore, because C5 is a late product of the classical and alternative complement pathways, inhibition of C5 is less likely to be associated with risks of concomitant infection that exist when targeting earlier products in the cascade (Allegretti, M., et al., Curr Med Chem, 2005. 12(2): p. 217-36).

The ability of an agent to bind C5 may be determined by standard in vitro assays known in the art, for example by western blotting following incubation of the protein on the gel with labelled C5. Preferably, the agent according to the invention binds C5 with an $IC_{50}$ of less than 0.2 mg/ml, preferably less than 0.1 mg/ml, preferably less than 0.05 mg/ml, preferably less than 0.04 mg/ml, preferably less than 0.03 mg/ml, preferably 0.02 mg/ml, preferably less than 1 μg/ml, preferably less than 100 ng/ml, preferably less than 10 ng/ml, more preferably still, less than 1 ng/ml.

Preferably, the agent that binds C5 is derived from a haematophagous arthropod. The term "haematophagous arthropod" includes all arthropods that take a blood meal from a suitable host, such as insects, ticks, lice, fleas and mites. Preferably, the agent is derived from a tick, preferably from the tick *Ornithodoros moubata*.

According to one embodiment of the invention, the agent that binds C5 is a protein comprising amino acids 19 to 168 of the amino acid sequence in FIG. 2 or is a functional equivalent of this protein. The agent that binds C5 may be a protein consisting of amino acids 19 to 168 of the amino acid sequence in FIG. 2 or be a functional equivalent of this protein.

According to an alternative embodiment, the protein used according to this embodiment of the invention may comprise or consist of amino acids 1 to 168 of the amino acid sequence in FIG. 2, or be a functional equivalent thereof. The first 18 amino acids of the protein sequence given in FIG. 2 form a signal sequence which is not required for C5 binding activity and so this may optionally be dispensed with, for example, for efficiency of recombinant protein production.

The protein having the amino acid sequence given in FIG. 2, also referred to herein as the EV576 protein, was isolated from the salivary glands of the tick *Ornithodoros moubata*. EV576 is an outlying member of the lipocalin family and is the first lipocalin family member shown to inhibit complement activation. The EV576 protein inhibits the alternative, classical and lectin complement pathways by binding C5 and preventing its cleavage by C5 convertase into Complement C5a and Complement C5b-9, thus inhibiting both the action of C5a peptide and the MAC. The term "EV576 protein", as used herein, refers to the sequence given in FIG. 2 with or without the signal sequence.

The EV576 protein and the ability of this protein to inhibit complement activation has been disclosed in WO2004/106369, where the EV576 protein was referred to as the "OmCI protein". It has now been found that the EV576 protein is surprisingly effective in the treatment and prevention of myasthenia gravis. The data presented herein demonstrate that a single injection of EV576 totally attenuates weight loss and muscular weakness in the EAMG in mice for at least 7 days. EV576 is thus more effective in the treatment and prevention of EAMG than sCR1 which, as discussed above, only reduced the clinical symptoms of myasthenia gravis when administered on a daily basis (Piddlesden et al, J. Neuroimmunol., 1996, 71: 173-177). The surprising effectiveness of EV576 in the treatment of myasthenia gravis appears to be due to the fact that it acts by binding C5, thus inhibiting the activity of C5a and MAC. In addition, the data presented herein demonstrate that rEV576 is effective in models of both early mild myasthenia gravis and severe late stage myasthenic crises.

According to a further embodiment of the invention, the agent may be a nucleic acid molecule encoding the EV576 protein or a functional equivalent thereof. For example, gene therapy may be employed to effect the endogenous production of the EV576 protein by the relevant cells in the subject, either in vivo or ex vivo. Another approach is the administration of "naked DNA" in which the therapeutic gene is directly injected into the bloodstream or into muscle tissue.

Preferably, such a nucleic acid molecule comprises or consists of bases 53 to 507 of the nucleotide sequence in FIG. 2.

This nucleotide sequence encodes the EV576 protein in FIG. 2 without the signal sequence. The first 54 bases of the nucleotide sequence in FIG. 2 encode the signal sequence of which is not required for complement inhibitory activity. Alternatively, the nucleic acid molecule may comprise or consist of bases 1 to 507 of the nucleic acid sequence in FIG. 2, which encodes the protein with the signal sequence.

The EV576 protein has been demonstrated to bind to C5 and prevent its cleavage by C5 convertase in rat, mouse and human serum with an $IC_{50}$ of approximately 0.02 mg/ml. Preferably, functional equivalents of the EV576 protein which retain the ability to bind C5 with an $IC_{50}$ of less than 0.2 mg/ml, preferably less than 0.1 mg/ml, preferably less than 0.05 mg/ml, preferably less than 0.02 mg/ml, preferably less than 1 μg/ml, preferably less than 100 ng/ml, preferably less than 10 ng/ml, more preferably still, less than 1 ng/ml.

The serum beta half-life of $^{125}$I labelled EV576 in rats has been found to be 30-38 hours. Preferably, the EV576 protein and its functional equivalents retain a half-life of greater than 20 hours, preferably greater than 25 hours, preferably greater than 30 hours, preferably greater than 40 hours, preferably greater than 50 hours, preferably greater than 100 hours.

In one respect, the term "functional equivalent" is used herein to describe homologues and fragments of the EV576 protein which retain its ability to bind C5, and to prevent the cleavage of complement C5 by C5 convertase into complement C5a and complement C5b-9. The term "functional equivalent" also refers to molecules that are structurally similar to the EV576 protein or that contain similar or identical tertiary structure, particularly in the environment of the active site or active sites of the EV576 protein that binds to C5, such as synthetic molecules.

The term "homologue" is meant to include reference to paralogues and orthologues of the EV576 sequence that is explicitly identified in FIG. 2, including, for example, the EV576 protein sequence from other tick species, including *Rhipicephalus appendiculatus, R. sanguineus, R. bursa, A. americanum, A. cajennense, A. hebraeum, Boophilus microplus, B. annulatus, B. decoloratus, Dermacentor reticulatus, D. andersoni, D. marginatus, D. variabilis, Haemaphysalis inermis, Ha. leachii, Ha. punctata, Hyalomma anatolicum anatolicum, Hy. dromedarii, Hy. marginatum marginatum, Ixodes ricinus, I. persulcatus, I. scapularis, I. hexagonus, Argas persicus, A. reflexus, Ornithodoros erraticus, O. moubata moubata, O. m. porcinus*, and *O. savignyi*. The term "homologue" is also meant to include the equivalent EV576 protein sequence from mosquito species, including those of the *Culex, Anopheles* and *Aedes* genera, particularly *Culex quinquefasciatus, Aedes aegypti* and *Anopheles gambiae*; flea species, such as *Ctenocephalides felis* (the cat flea); horseflies; sandflies; blackflies; tsetse flies; lice; mites; leeches; and flatworms. The native EV576 protein is thought to exist in *O. moubata* in another three forms of around 18 kDa and the term "homologue" is meant to include these alternative forms of EV576.

Methods for the identification of homologues of the EV576 sequence given in FIG. 2 will be clear to those of skill in the art. For example, homologues may be identified by homology searching of sequence databases, both public and private. Conveniently, publicly available databases may be used, although private or commercially-available databases will be equally useful, particularly if they contain data not represented in the public databases. Primary databases are the sites of primary nucleotide or amino acid sequence data deposit and may be publicly or commercially available. Examples of publicly-available primary databases include the GenBank database (www.ncbi.nlm.nih.gov/), the EMBL database (www.ebi.ac.uk/), the DDBJ database (www.ddbj.nig.ac.jp/), the SWISS-PROT protein database (expasy.hcuge.ch/), PIR (pir.georgetown.edu/), TrEMBL (www.ebi.ac.uk/), the TIGR databases (see www.tigr.org/tdb/index.html), the NRL-3D database (www.nbrfa.georgetown.edu), the Protein Data Base (www.rcsb.org/pdb), the NRDB database (ncbi.nlm.nih.gov/pub/nrdb/README), the OWL database (www.biochem.ucl.ac.uk/bsm/dbbrowser/OWL/) and the secondary databases PROSITE (expasy.hcuge.ch/sprot/prosite.html), PRINTS (iupab.leeds.ac.uk/bmb5dp/prints. html), Profiles (ulrec3.unil.ch/software/PFSCAN_form.html), Pfam (www.sanger.ac.uk/software/pfam), Identify (dna.stanford.edu/identify/) and Blocks (www.blocks.fhcrc.org) databases. Examples of commercially-available databases or private databases include PathoGenome (Genome Therapeutics Inc.) and PathoSeq (Incyte Pharmaceuticals Inc.).

Typically, greater than 30% identity between two polypeptides (preferably, over a specified region such as the active site) is considered to be an indication of functional equivalence and thus an indication that two proteins are homologous. Preferably, proteins that are homologues have a degree of sequence identity with the EV576 protein sequence identified in FIG. 2 of greater than 60%. More preferred homologues have degrees of identity of greater than 70%, 80%, 90%, 95%, 98% or 99%, respectively with the EV576 protein sequence given in FIG. 2. Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Homologues of the EV576 protein sequence given in FIG. 2 include mutants containing amino acid substitutions, insertions or deletions from the wild type sequence, for example, of 1, 2, 3, 4, 5, 7, 10 or more amino acids, provided that such mutants retain the ability to bind C5. Mutants thus include proteins containing conservative amino acid substitutions that do not affect the function or activity of the protein in an adverse manner. This term is also intended to include natural biological variants (e.g. allelic variants or geographical variations within the species from which the EV576 proteins are derived). Mutants with improved ability to bind C5 may also be designed through the systematic or directed mutation of specific residues in the protein sequence.

Fragments of the EV576 protein and of homologues of the EV576 protein are also embraced by the term "functional equivalents" providing that such fragments retain the ability to bind C5. Fragments may include, for example, polypeptides derived from the EV576 protein sequence which are less than 150 amino acids, less than 125 amino acids, less than 100 amino acids, less than 75 amino acids, less than 50 amino acids, or even 25 amino acids or less, provided that these fragments retain the ability to bind to complement C5. Included as such fragments are not only fragments of the *O. moubata* EV576 protein that is explicitly identified herein in FIG. 2, but also fragments of homologues of this protein, as described above. Such fragments of homologues will typically possess greater than 60% identity with fragments of the EV576 protein sequence in FIG. 2, although more preferred fragments of homologues will display degrees of identity of greater than 70%, 80%, 90%, 95%, 98% or 99%, respectively with fragments of the EV576 protein sequence in FIG. 2. Fragments with improved may, of course, be rationally designed by the systematic mutation or fragmentation of the wild type sequence followed by appropriate activity assays. Fragments may exhibit similar or greater affinity for C5 as EV576 and may have the same or greater $IC_{50}$ for C5.

A functional equivalent used according to the invention may be a fusion protein, obtained, for example, by cloning a polynucleotide encoding the EV576 protein in frame to the coding sequences for a heterologous protein sequence. The term "heterologous", when used herein, is intended to designate any polypeptide other than the EV576 protein or its functional equivalent. Example of heterologous sequences, that can be comprised in the soluble fusion proteins either at N- or at C-terminus, are the following: extracellular domains of membrane-bound protein, immunoglobulin constant regions (Fc region), multimerization domains, domains of extracellular proteins, signal sequences, export sequences, or sequences allowing purification by affinity chromatography. Many of these heterologous sequences are commercially available in expression plasmids since these sequences are commonly included in the fusion proteins in order to provide additional properties without significantly impairing the specific biological activity of the protein fused to them (Terpe K, Appl Microbiol Biotechnol, 60: 523-33, 2003). Examples of such additional properties are a longer lasting half-life in body fluids, the extracellular localization, or an easier purification procedure as allowed by a tag such as a histidine or HA tag.

The EV576 protein and functional equivalents thereof, may be prepared in recombinant form by expression in a host cell. Such expression methods are well known to those of skill in the art and are described in detail by Sambrook et al (2000) and Fernandez & Hoeffler (1998). Recombinant forms of the EV576 protein and functional equivalents thereof are preferably unglycosylated.

The proteins and fragments of the present invention can also be prepared using conventional techniques of protein chemistry. For example, protein fragments may be prepared by chemical synthesis. Methods for the generation of fusion proteins are standard in the art and will be known to the skilled reader. For example, most general molecular biology, microbiology recombinant DNA technology and immunological techniques can be found in Sambrook et al. (2000) or Ausubel et al. (1991).

The subject to Which the agent that binds C5 is administered in the method or use of the invention is preferably a mammal, preferably a human. The subject to which the agent that binds C5 is administered may also be suffering from a further disease with which myasthenia gravis is associated, such as a thymic tumor, thyrotoxicosis, rheumatoid arthritis and lupus erythematosus.

The agent is administered in a therapeutically or prophylactically effective amount. The term "therapeutically effective amount" refers to the amount of agent needed to treat or ameliorate a targeted disease. The term "prophylactically effective amount" used herein refers to the amount of agent needed to prevent a targeted disease.

Preferably, the dose of the agent is sufficient to bind as much available C5 as possible in the subject, more preferably, all available C5. Preferably, the dose of the agent supplied is at least twice the molar dose needed to bind all available C5 in the subject. The dose of the agent supplied may be 2.5 times, 3 times or 4 times the molar dose needed to bind all available C5 in the subject. In one embodiment, the dose is from 1 mg/kg to 15 mg/kg. Preferably, the dose is from 1 mg/kg (mass of drug compared to mass of patient) to 10 mg/kg, preferably 2 mg/kg to 8 mg/kg.

The frequency with which the dose needs to be administered will depend on the half-life of the agent involved. Where the agent is the EV576 protein or a functional equivalent thereof, the dose may be administered on a daily basis, a twice daily basis, or every two, three, four days, five, six, seven, 10, 15 or 20 days or more.

The exact dosage and the frequency of doses may also be dependent on the patient's status at the time of administration. Factors that may be taken into consideration when determining dosage include the severity of the disease state in the patient, the general health of the patient, the age, weight, gender, diet, time and frequency of administration, drug combinations, reaction sensitivities and the patient's tolerance or response to therapy. The precise amount can be determined by routine experimentation, but may ultimately lie with the judgement of the clinician.

The agent will generally be administered as part of a pharmaceutically acceptable carrier. The term "pharmaceutically acceptable carrier", as used herein, includes genes, polypeptides, antibodies, liposomes, polysaccharides, polylactic acids, polyglycolic acids and inactive virus particles or indeed any other agent provided that the carrier does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in Remington's Pharmaceutical Sciences (Mack Pub. Co., N.J. 1991).

The agent may be delivered by any known route of administration. The agent may be delivered by a parenteral route (e.g. by injection, either subcutaneously, intraperitoneally, intravenously or intramuscularly or delivered to the interstitial space of a tissue). The compositions can also be administered into a lesion. Other modes of administration include oral and pulmonary administration, suppositories, and transdermal or transcutaneous applications, needles, and hyposprays.

The agent that binds C5 may be administered alone or as part of a treatment regimen also involving the administration of other drugs currently used in the treatment of patients with myasthenia gravis. For example, the agent may be administered in combination with anticholinesterase agents, such as neostigmine and pyridostigmine, or immunosuppressive drugs, such as prednisone, cyclosporine, and azathioprine. Combinations of drug treatments may have an additive or synergistic effect on treatment of the disease.

The invention thus provides (i) an agent that binds C5, preferably the EV576 protein or a functional equivalent thereof, and (ii) an anticholinesterase agent and/or an immunosuppressive drug, for use in therapy.

The invention also provides the use of—(i) an agent that binds C5, preferably the EV576 protein or a functional equivalent thereof, and (ii) an anticholinesterase agent and/or an immunosuppressive drug, in the manufacture of a medicament for treating myasthenia gravis.

The agent that binds C5 may be administered simultaneously, sequentially or separately with the other drug(s). For example, the agent that binds C5 may be administered before or after administration of the other drug(s).

The invention thus provides the use of an agent that binds C5, preferably the EV576 protein or a functional equivalent thereof, in the manufacture of a medicament for treating myasthenia gravis in a subject, wherein said subject has been pre-treated with an anticholinesterase agent and/or an immunosuppressive drug. The invention also provides the use of an anticholinesterase agent and/or an immunosuppressive drug in the manufacture of a medicament for treating myasthenia gravis in a subject wherein said subject has been pre-treated with an agent that binds C5, preferably the EV576 protein or a functional equivalent thereof.

The agent that binds C5 may also be administered as part of a treatment regimen also involving the administration of other drugs currently used in the treatment of other diseases with which myasthenia gravis is associated, such as a thymic tumor, thyrotoxicosis, rheumatoid arthritis and lupus erythematosus. The agent that binds C5 may be administered simultaneously, sequentially or separately with the other drug(s). For example, the agent that binds C5 may be administered before or after administration of the other drug(s).

Various aspects and embodiments of the present invention will now be described in more detail by way of example. It will be appreciated that modification of detail may be made without departing from the scope of the invention.

BRIEF DESCRIPTION OF FIGURES

FIG. 2: Primary sequence of EV576. Signal sequence underlined. Cysteine residues in bold type. Nucleotide and amino acid number indicated at right. The nucleic and amino acid sequences presented therein are designated SEQ ID NO: 1 and SEQ ID NO: 2, respectively.

EXAMPLES

1. Mechanism of Action and Inhibitory Concentration.

Figure 1:
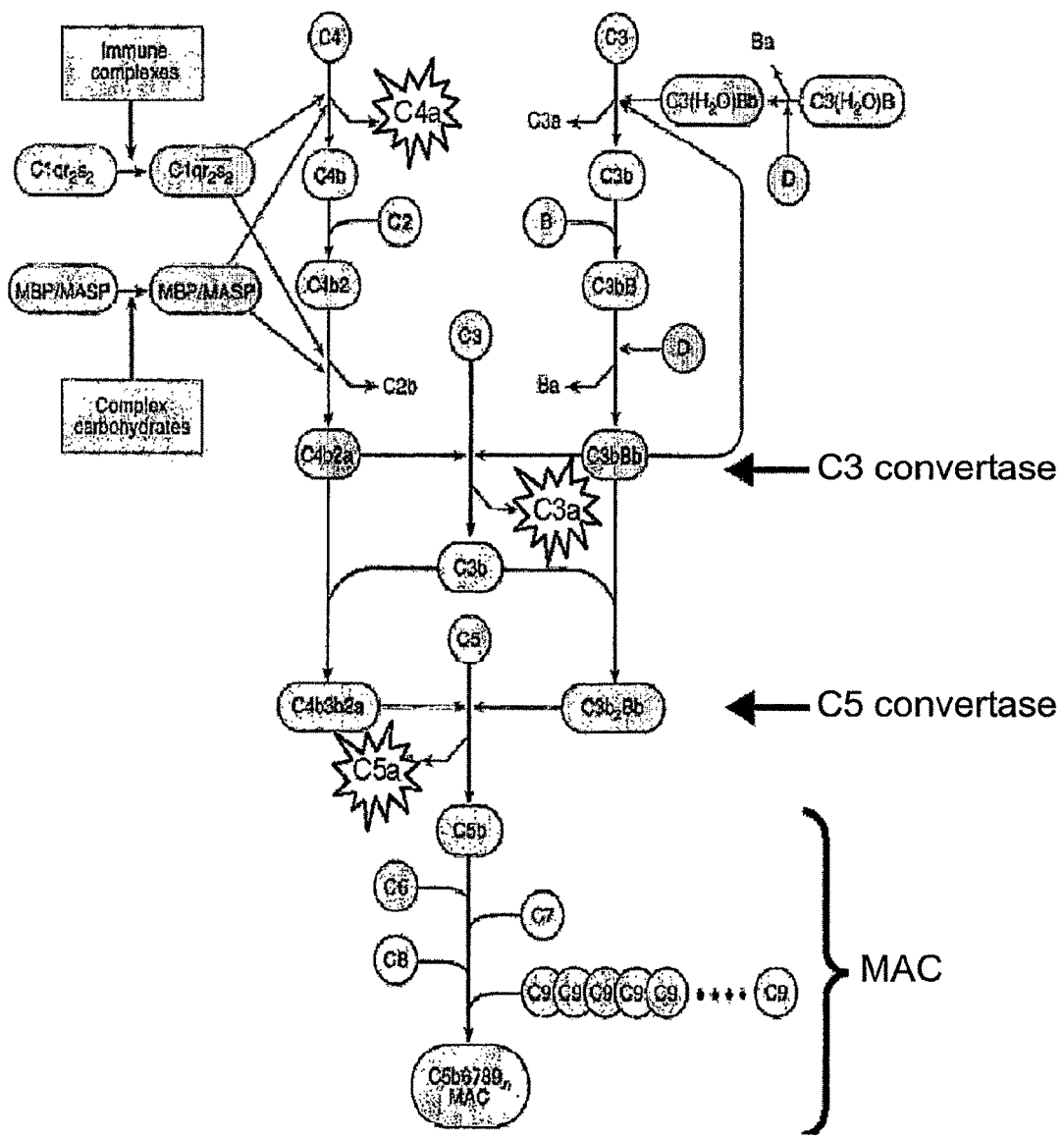
FIG. 1: Schematic diagram of classical and alternative pathways of complement activation. Enzymatic components, dark grey. Anaphylatoxins enclosed in starbursts.
Figure 3A:
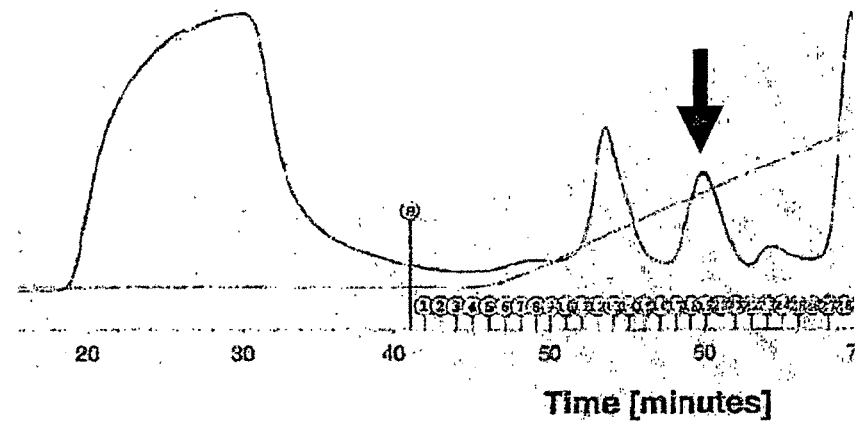
FIG. 3: Purification of EV576 from tick salivary gland extract (SGE). A) Anion exchange chromatography. B) Classical haemolytic assay of fractions. C) Reducing SDS-PAGE. D) reverse phase high performance liquid chromatography (RP-HPLC).
Figure 3B:
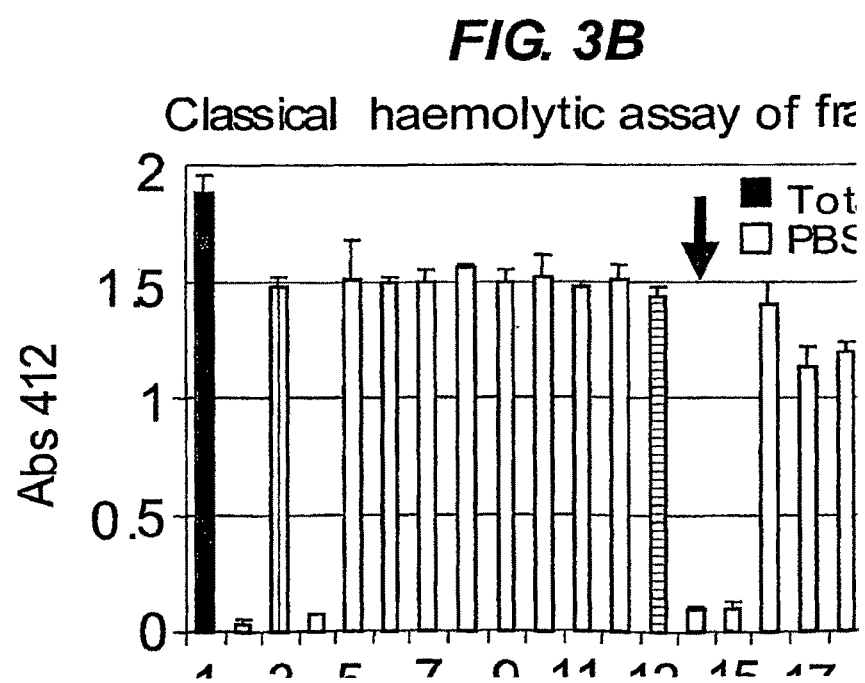

EV576 was purified from salivary gland extracts of the soft tick *Orthinodoros moubata* by SDS-PAGE and RP-HPLC of fractions of salivary gland extract found to contain complement inhibitory activity by classical haemolytic assays (FIG. 3) as disclosed in WO2004/106369.

Figure 4A:
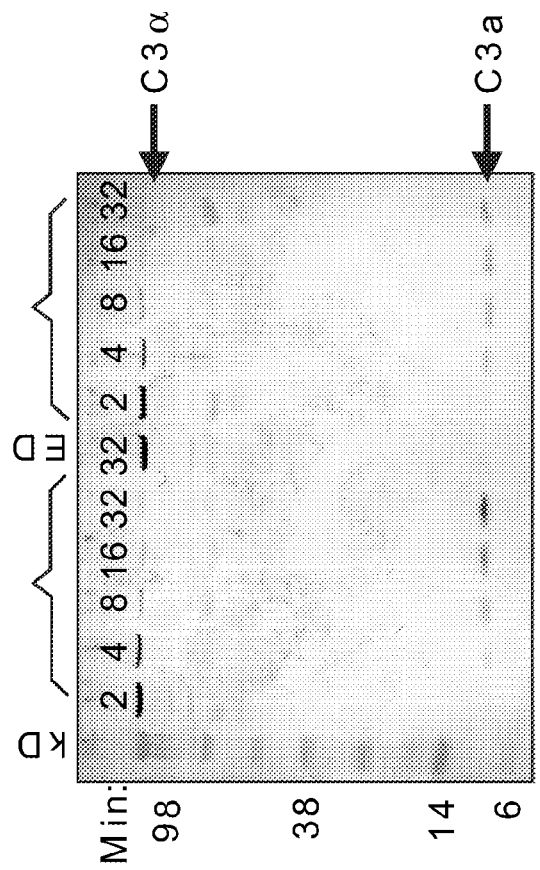
FIG. 4: Mechanism of action of EV576. A) No effect on C3a production. This presents a time course for a classical haemolytic assay; the immunoblot is probed with human anti-C3a antibody. B) Prevents C5a production. C5a in the haemolytic assays was measured using an ELISA kit. C) Binds directly to C5. EV 576 and control (RaHBP2) were transferred to nitrocellulose and probed with radiolabelled C3 and C5.
Figure 4B:
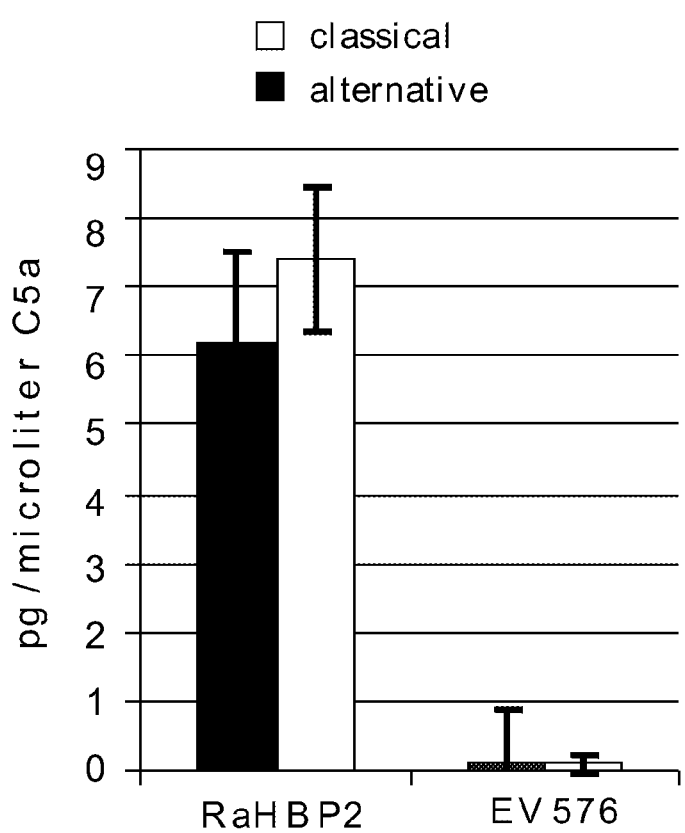

EV576 inhibits both human and guinea pig classical and alternative pathways. It has no effect on the rate of C3a production (FIG. 4A) but prevents cleavage of C5a from C5 (FIG. 4B).

Figure 4C:
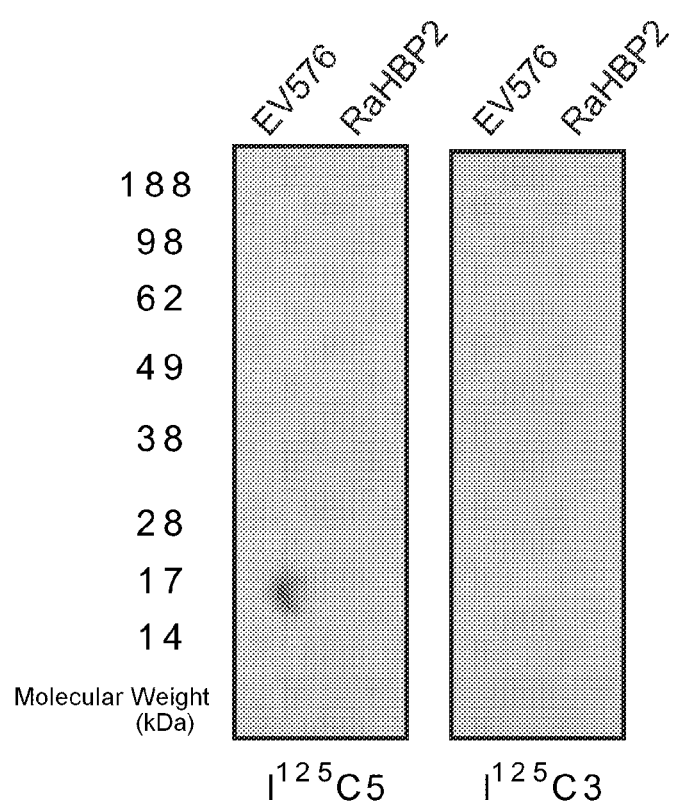

The ability of EV576 to inhibit both the classical and the alternative complement pathways is due to binding of the molecule to complement C5, the precursor of C5a and C5b-9. EV576 binds directly to C5 (FIG. 4C) with an $IC_{50}$ of ≈0.02 mg/ml. The precise binding mechanism and accessory roles (if any) played by serum factors are under investigation.

Figure 5B:
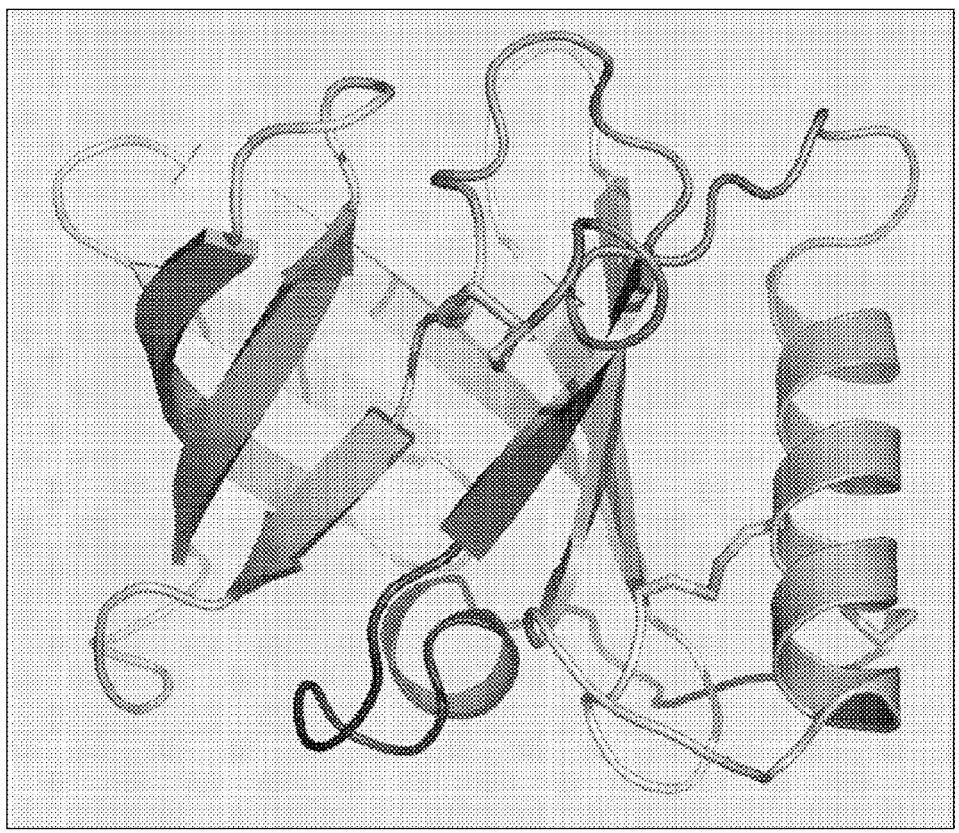
FIG. 5: Recombinant EV576. A) Recombinant EV576 (rEV576) inhibits complement as effectively as native EV576. Activity of recombinant and native protein are indicated. B) Structure of EV576. EV576 is an outlying member of the lipocalin family. It has 46% amino acid identity with moubatin, a platelet aggregation inhibitor from *O. moubata*.

Recombinant EV576 (rEV576) with glycosylation sites removed (which otherwise are glycosylated in the yeast expression system) is as active as the native non-glycosylated protein (FIG. 5A).

The structure of EV576 confirms that it is an outlying member of the lipocalin family (FIG. 5B), having 46% identity with moubatin, a platelet aggregation inhibitor from *O. moubata*. Lipocalins are a large group of soft tick proteins the functions of which, with rare exceptions, are unknown.

2. Half-Life.

The serum beta half-life of $^{125}$I labelled rEV576 in rats was found to be ≈30-38 hours.

3. Effect of EV576 on Experimental Autoimmune Myasthenia Gravis.

Experiment 1

Experimental autoimmune myasthenia gravis (EAMG) was induced in female Lewis rats according to the method of Piddlesden et al. (supra).

Lewis rats were injected with 1 mg/kg anti-AchR mAb35 intraperitoneally at day 0, along with either: i) 3.25 mg rEV576 (calculated to be 2.5× the molar dose needed to bind all available C5); or ii) phosphate buffered saline (PBS). The rats were assessed for changes in weight and clinical score over 7 days. (FIG. 6).

Injection of 3.25 mg rEV576 totally attenuated mAb35 induced weight loss and muscular weakness compared to control.

Figure 6A:
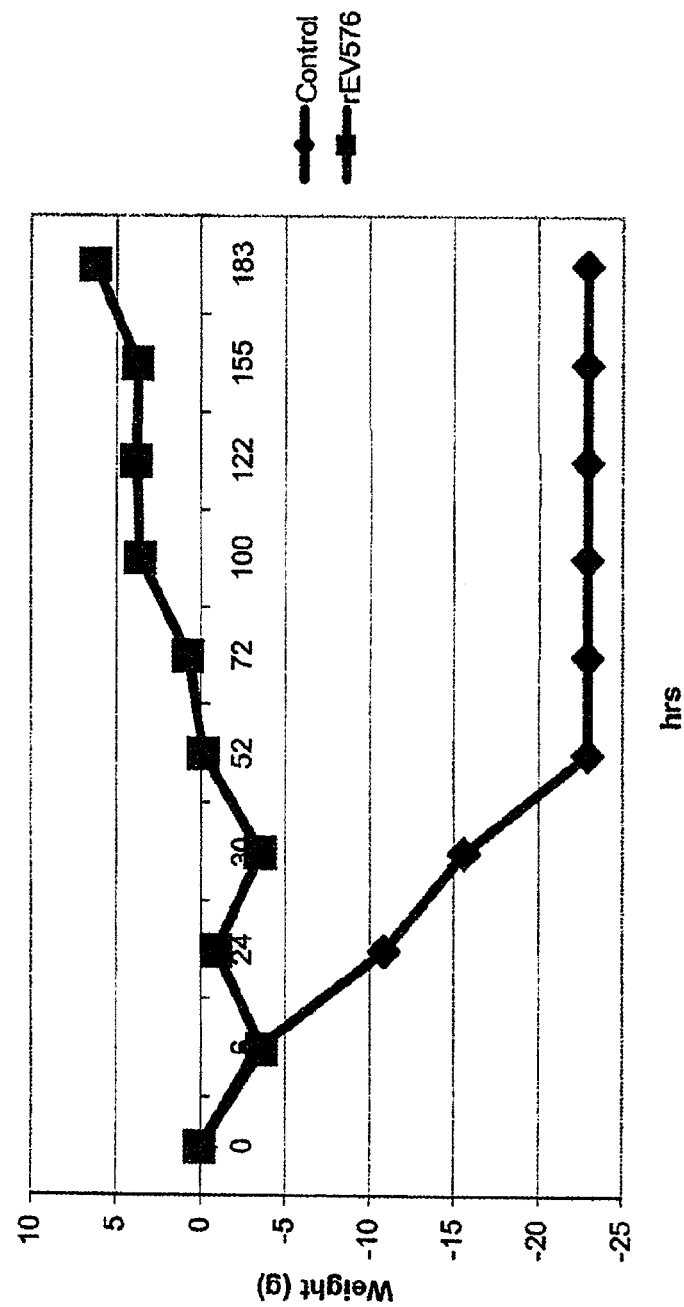
FIG. 6: Effect of rEV576 in experimental myasthenia gravis model. A) rEV576 prevents weight loss compared with control animals. Weight change is shown. B) Clinical scores in animals treated with rEV576 compared with control animals. Mean assessment of clinical score is shown. C) Raw data for clinical scores. All animals in control group A sacrificed at 72 h by schedule 1 following onset of severe clinical EAMG.
Figure 6B:
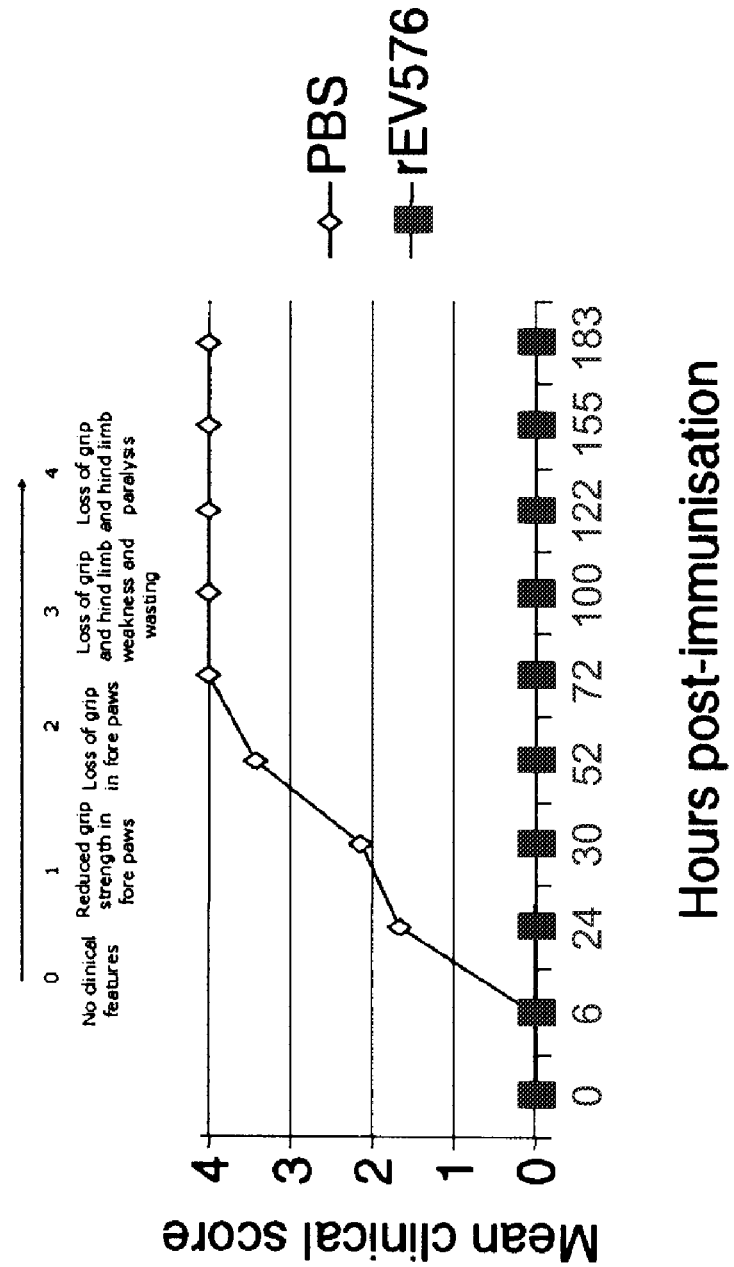

All control animals became moribund and had to be euthanased at 72 hours post-induction whereas all rEV576 treated animals survived, gained weight and showed no muscle weakness for the duration of the experiment (183 hours) (FIG. 6).

A single injection of rEV576 thus completely attenuates the symptoms of EAMG for at least 7 days.

Experiment 2 rEV576 was further analysed in a chronic model of EAMG. In this model, animals receive acetylcholine receptor protein in Complete Freund's Adjuvant (CFA) and generate their own antibodies over the course of approximately 30 days. This model mimics the human condition where symptoms occur and progress relatively slowly.

18 Lewis rats were immunised by subcutaneous injection of purified acetylecholine receptor protein (2×20 µg in 100 µl of PBS emulsified in equal volume of complete Freund's adjuvant+nonviable Mycobacterium tuberculosis–0.5 mg). Control rats were injected with PBS only.

After the onset of disease (EAMG clinical score 1 or 2 and weight loss<15%) 9 rats were injected with 3.25 mg of rEV576 i.p. and treatment continued for 10 days with 1 mg for every 12 hrs. Out of these nine rats, three rats were assessed as having severe myasthenia (S-EAMG) and six rats as having mild myasthenia (M-EAMG).

The remaining 9 rats were untreated. Out of these nine rats, four rats were assessed as having severe myasthenia (S-EAMG) and five rats as having mild myasthenia (M-EAMG).

The two sets of rats were each assessed for changes in weight, grip strength and clinical score over 10 days.

Figure 7A:
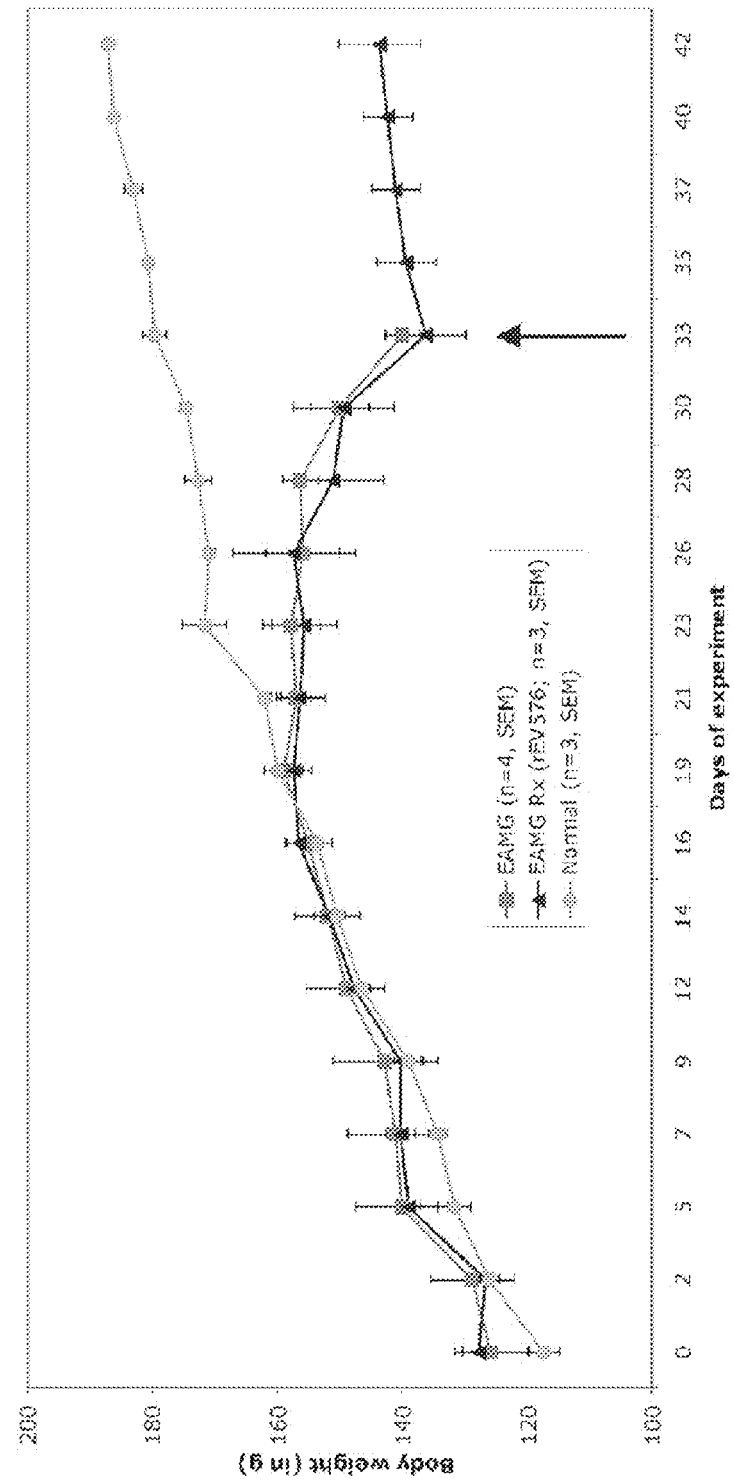
FIG. 7: Effect of rEV576 in chronic experimental myasthenia gravis model. A) In animals with severe experimental autoimmune myasthenia gravis (EAMG), rEV576 prevents weight loss and death compared with control animals. B) In animals with severe EAMG, rEV576 treatment gives significant improvement in clinical score and grip strength compared with control animals. rEV576 prevents strength loss in severe EAMG. C) In animals with mild EAMG, rEV576 prevents weight loss compared with control animals.
Figure 7B:
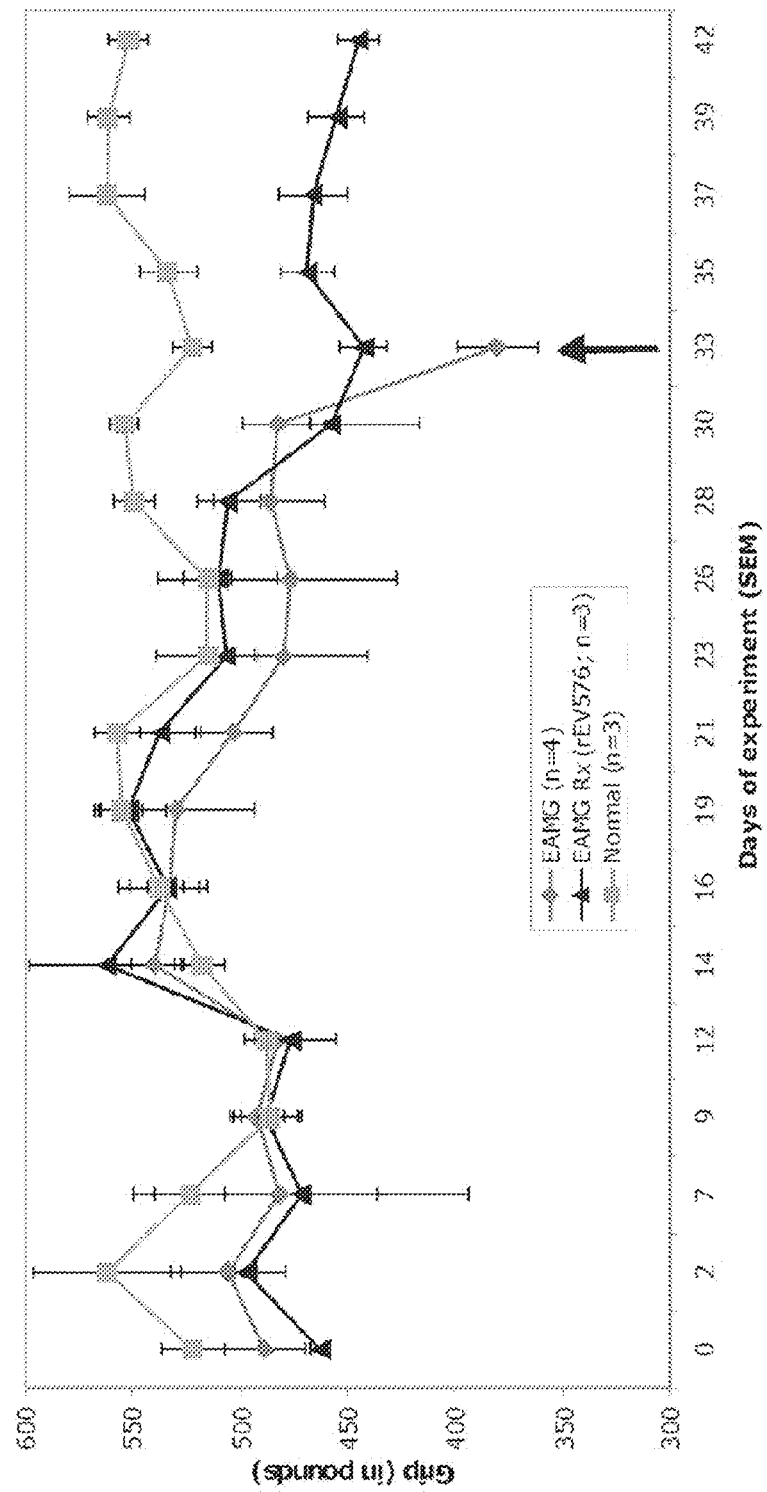

The rats in the severe EAMG group had lost 12% of their body weight and were within 24 hours of death when treatment with rEV576 was started. Untreated rats all died within 24 hours. The rEV576 treated rats showed a significant reduction in weight loss. At the beginning of treatment with rEV576 on Day 33, the average clinical score was 2.0. Injection of rEV576 for 10 days reduced the severity of clinical symptoms and prevented further weight loss (FIG. 7A). These rats also showed significant improvement in grip strength (FIG. 7B).

Figure 7C:
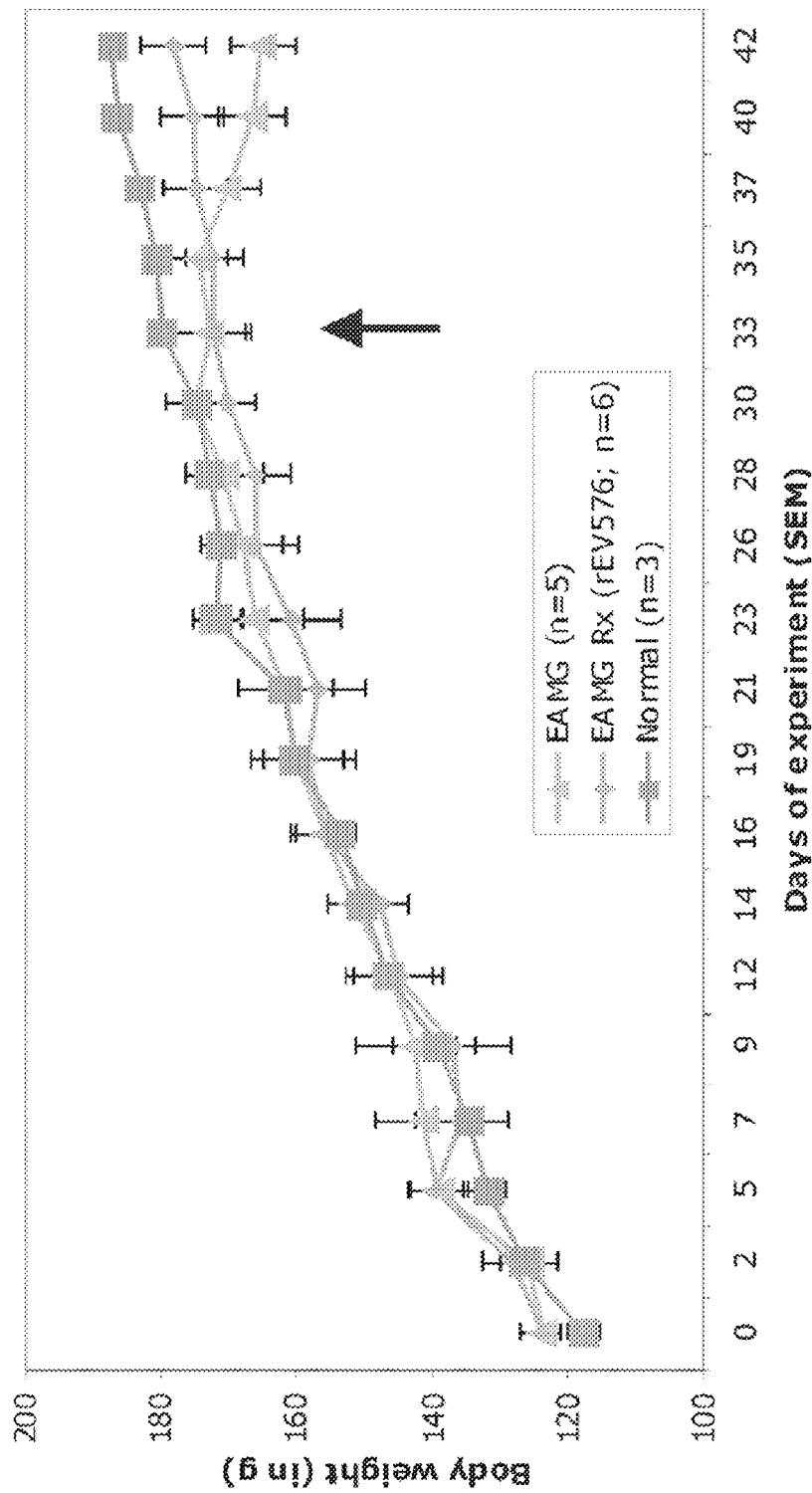

In rats exhibiting the mild early stage of EAMG, clinical signs were just starting and weight was just starting to decrease at Day 33. Weight loss was prevented in rats treated with rEV576 and rats gained in average about 3.43% of body weight. Untreated animals with identical clinical scores lost about 4.59% of body weight (FIG. 7C). There was no improvement in grip strength in treated compared with untreated rats exhibiting the mild early stage of EAMG (results not shown).

Figure 8A:
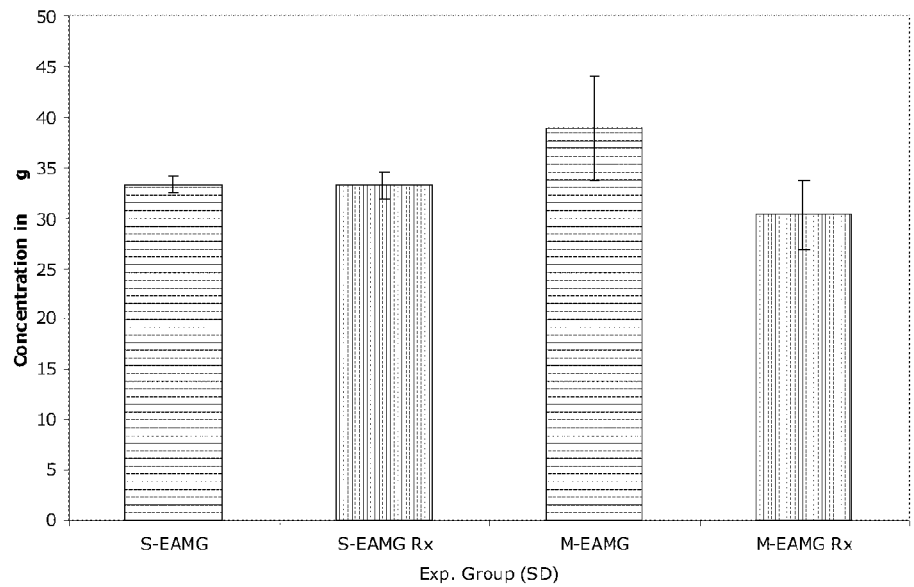
FIG. 8: Effect of rEV576 in chronic experimental myasthenia gravis model. A) AchR antibodies showed no differences between treated, untreated, mild EAMG or severe EAMG groups. AChR abs (ELISA) is shown. B) total complement hemolytic activity of rat serum from rats exhibiting both severe and mild EAMG. Total haemolytic activity in rat serum is shown.
Figure 8B:
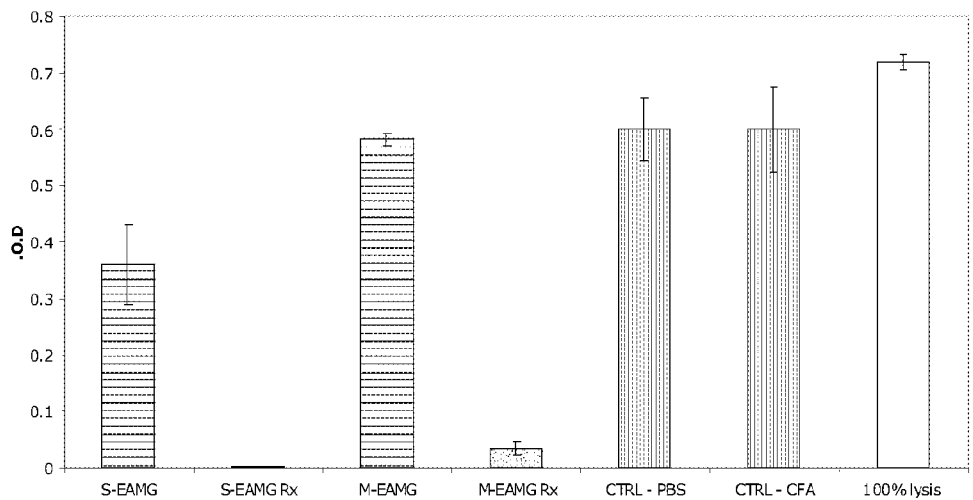

Blood was collected from the rats for the detection of AchR antibodies and an assessment of complement hemolytic activity. There was no difference between experimental groups in the AchR antibodies detected by direct ELISA (FIG. 8A). Rat serum from rats exhibiting both severe and mild EAMG which were treated with rEV576 completely inhibited complement activity (FIG. 8B).

Figure 9A:
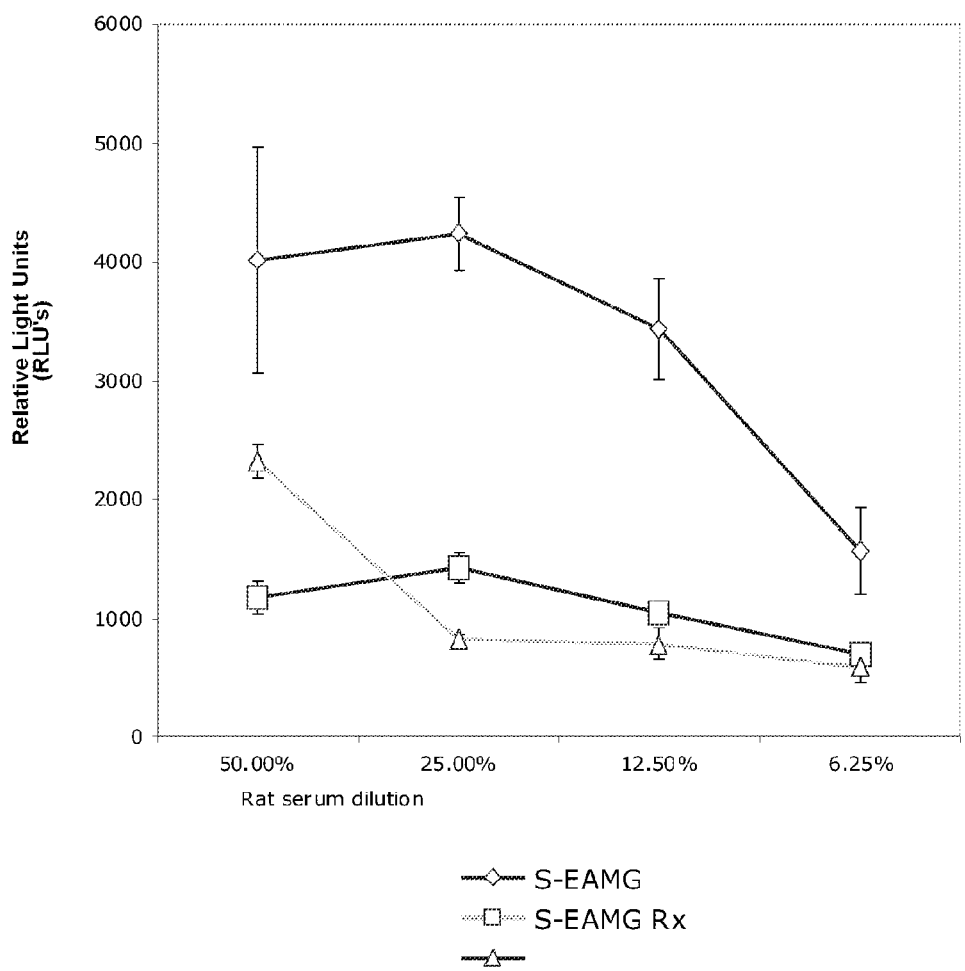
FIG. 9: Effect of rEV576 in chronic experimental myasthenia gravis model. A) Cytotoxicity of rat serum from rats exhibiting severe EAMG. Cytotoxicity of rat serum in severe-EAMG is shown (bckg 370.87 RLU's, 100% lysis 11282 RLU's). B) Cytotoxicity of rat serum from rats exhibiting mild EAMG. Cytotoxicity of rat serum in mild EAMG is shown (bckg 727 RLU's 100% lysis 8118 RLU's.
Figure 9B:
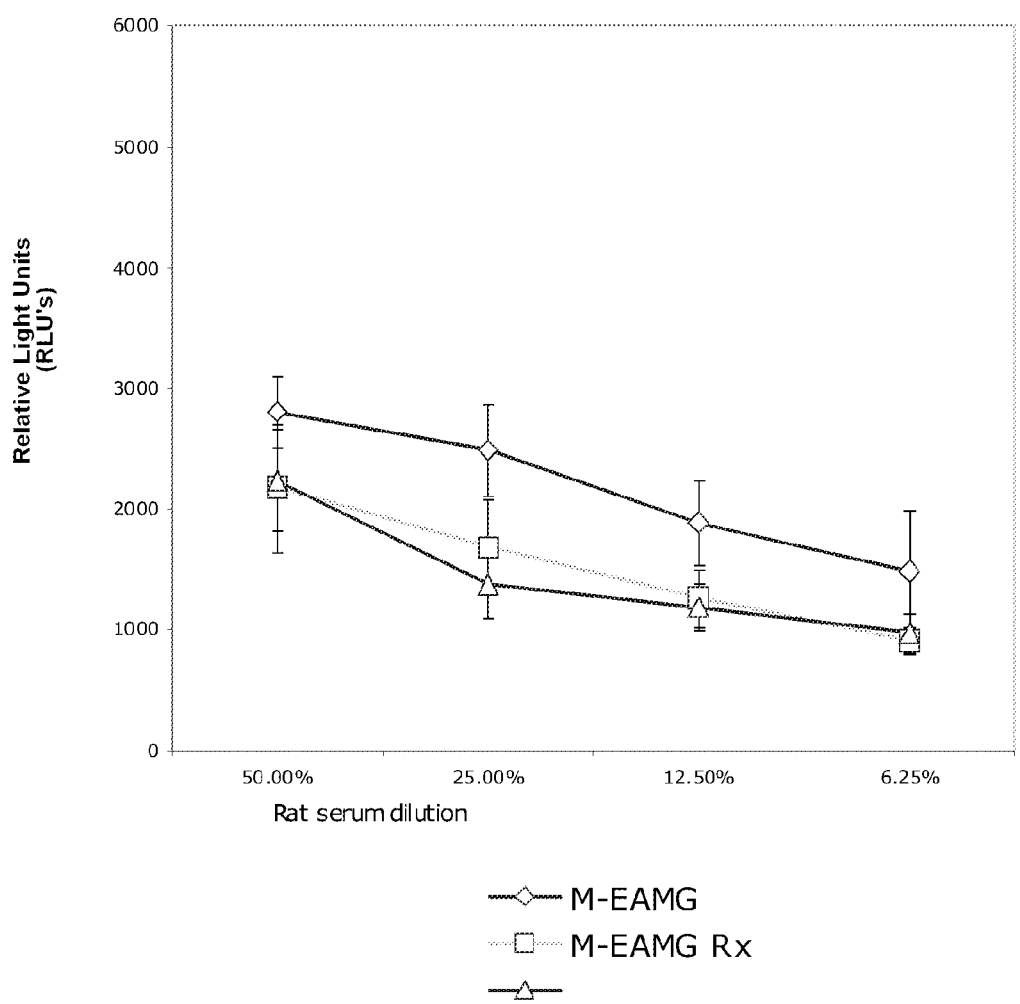

In addition, the cytotoxicity of rat serum from rats exhibiting both severe and mild EAMG was measured on rhabdomyosarcoma cell line (ATCC, CCL-136) using a ToxiLight Bioassay Kit. As can be seen in FIGS. 9A and 9B, the highest cytotoxicity was detected in untreated rats with severe EAMG. Animals treated with rEV576 showed a significant decrease in cytotoxic activity.

This data suggests that rEV576 may be effective in treating both early mild myasthenia gravis and severe late stage disease (eg myasthenic crises).

The invention claimed is:

1. A method of treating myasthenia gravis comprising administering subcutaneously to a human subject in need thereof a therapeutically effective amount of an agent that binds complement C5 protein, wherein the agent is:
  (a) a protein comprising or consisting of the amino acid sequence of SEQ ID NO: 2;
  (b) a protein comprising or consisting of amino acids 19 to 168 of SEQ ID NO: 2;
  (c) a protein comprising or consisting of an amino acid sequence having at least 95% sequence identity to amino acids 19 to 168 of SEQ ID NO: 2; or
  (d) a fragment of SEQ ID NO: 2, wherein said fragment comprises six cysteine residues that are spaced relative to each other at a distance of 32 amino acids apart, 62 amino acids apart, 28 amino acids apart, 1 amino acid apart, and 21 amino acids apart, respectively, as arranged from the amino terminus to the carboxyl terminus of SEQ ID NO: 2, wherein said fragment inhibits cleavage of C5 by classical and alternative C5 convertases.

2. The method according to claim 1, wherein the agent binds complement C5 protein with an $IC_{50}$ of less than 0.2 mg/ml.

3. A The method according to claim 1, wherein the agent is derived from a haematophagous arthropod.

4. The method according to claim 1, wherein the therapeutically effective amount is a dose from 1 mg/kg to 15 mg/kg.

5. The method according to claim 1, wherein the agent is administered as part of a treatment regimen also involving the administration of a further drug for the treatment of myasthenia gravis.

6. The method according to claim 5, wherein the further drug is an anticholinesterase agent, neostigmine, or pyridostigmine, or an immunosuppressive drug, prednisone, cyclosporine, or azathioprine.

7. The method according to claim 5, wherein the agent is administered simultaneously with the further drug.

8. The method according to claim 5, wherein the agent is administered sequentially with the further drug.

9. The method according to claim 5, wherein the agent is administered separately with the further drug.

10. The method according to claim 1, wherein the myasthenia gravis is mild myasthenia gravis.

11. The method according to claim 1, wherein the myasthenia gravis is severe myasthenia gravis.

12. The method according to claim 1, wherein the therapeutically effective amount is a dose from 1 mg/kg to 10 mg/kg.

13. The method according to claim 1, wherein the therapeutically effective amount is a dose from 2 mg/kg to 8 mg/kg.

14. The method according to claim 1, wherein the agent is administered on a daily basis.

* * * * *

SEQUENCE LISTING

```
<160> NUMBER OF SEQ ID NOS: 2

<210> SEQ ID NO 1
<211> LENGTH: 507
<212> TYPE: DNA
<213> ORGANISM: Orthinodoros moubata

<400> SEQUENCE: 1
atgctggttt tggtgaccct gatttctcc ttttctgcga acatcgcata tgctgacagc      60
gaaagcgact gcactggaag cgaacctgtt gacgccttcc aagctttcag tgagggcaaa     120
gaggcatatg tcctggtgag gtccacggat cccaaagcga gggactgctt gaaaggagaa     180
ccagccggag aaaagcagga caacacgttg ccggtgatga tgacgtttaa gaatggcaca     240
gactgggctt caaccgattg gacgtttact ttggacggcg caaaggtaac ggcaaccctt     300
ggtaacctaa cccaaaatag ggaagtggtc tacgactcgc aaagtcatca ctgccacgtt     360
gacaaggtcg agaaggaagt tccagattat gagatgtgga tgctcgatgc gggagggctt     420
gaagtggaag tcgagtgctg ccgtcaaaag cttgaagagt tggcgtctgg caggaaccaa     480
atgtatcccc atctcaagga ctgctag                                         507

<210> SEQ ID NO 2
<211> LENGTH: 168
<212> TYPE: PRT
<213> ORGANISM: Orthinodoros moubata

<400> SEQUENCE: 2

Met Leu Val Leu Val Thr Leu Ile Phe Ser Phe Ser Ala Asn Ile Ala
1               5                   10                  15

Tyr Ala Asp Ser Glu Ser Asp Cys Thr Gly Ser Glu Pro Val Asp Ala
            20                  25                  30
```

```
Phe Gln Ala Phe Ser Glu Gly Lys Glu Ala Tyr Val Leu Val Arg Ser
        35              40                  45
Thr Asp Pro Lys Ala Arg Asp Cys Leu Lys Gly Glu Pro Ala Gly Glu
    50              55                  60
Lys Gln Asp Asn Thr Leu Pro Val Met Met Thr Phe Lys Asn Gly Thr
65              70                  75                      80
Asp Trp Ala Ser Thr Asp Trp Thr Phe Thr Leu Asp Gly Ala Lys Val
            85                  90                  95
Thr Ala Thr Leu Gly Asn Leu Thr Gln Asn Arg Glu Val Val Tyr Asp
            100             105                 110
Ser Gln Ser His His Cys His Val Asp Lys Val Glu Lys Glu Val Pro
        115             120                 125
Asp Tyr Glu Met Trp Met Leu Asp Ala Gly Gly Leu Glu Val Glu Val
    130             135                 140
Glu Cys Cys Arg Gln Lys Leu Glu Glu Leu Ala Ser Gly Arg Asn Gln
145             150                 155                     160
Met Tyr Pro His Leu Lys Asp Cys
            165
```